United States Patent
Tomita et al.

(10) Patent No.: US 7,435,488 B2
(45) Date of Patent: Oct. 14, 2008

(54) FINE STRUCTURAL BODY AND METHOD OF PRODUCING THE SAME

(75) Inventors: Tadabumi Tomita, Shizuoka (JP); Yoshinori Hotta, Aichi (JP); Akio Uesugi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 476 days.

(21) Appl. No.: 11/086,368

(22) Filed: Mar. 23, 2005

(65) Prior Publication Data

US 2005/0211566 A1 Sep. 29, 2005

(30) Foreign Application Priority Data

| Mar. 23, 2004 | (JP) | ............................... 2004-084071 |
| May 26, 2004 | (JP) | ............................... 2004-156154 |

(51) Int. Cl.
*G11B 5/66* (2006.01)
*B32B 9/04* (2006.01)

(52) U.S. Cl. .................... 428/702; 428/846.4; 427/275; 427/129; 427/327

(58) Field of Classification Search ........................ None
See application file for complete search history.

(56) References Cited

U.S. PATENT DOCUMENTS

| 4,925,738 A * | 5/1990 | Tsuya et al. ............. 428/846.4 |
| 5,139,884 A * | 8/1992 | Daimon et al. ........... 428/846.4 |
| 5,747,180 A | 5/1998 | Miller et al. |
| 7,079,250 B2 * | 7/2006 | Mukai ........................ 356/445 |

| 2003/0020060 A1 | 1/2003 | Iwasaki et al. |

FOREIGN PATENT DOCUMENTS

| EP | 1016621 A2 | 7/2000 |
| EP | 1445601 A2 | 8/2004 |
| JP | 2000-356587 A | 12/2000 |
| JP | 2003-268592 A | 9/2003 |

OTHER PUBLICATIONS

English abstract of JP 2000-31462, Japan, Jan. 28, 2000.*
Masuda, Hideki, "Highly ordered metal nanohole arragys based on anodized alumina", Solid State Physics, 1996 vol. 31, No. 5, pp. 496-497.*
H. Masuda et al., "Self Ordering of Cell Configuration of Anodic Porous Alumina with Large Size Pores in Phosphoric Acid Solution" Japanese Journal of Applied Physics, Nov. 1, 1998, vol. 37 p. L1340-1342.
Okamoto, Takayuki, "Researches on Interaction of Metal Nanoparticles and on Biosensors".
H. Masuda et al., "Self Ordering of Cell Arrangement of Anodic Porous Alumina with Formed Acid Solution", The Electrochemical Society, vol. 144 No. 5, May 1997, p. 127-130.

(Continued)

*Primary Examiner*—Holly Rickman
(74) *Attorney, Agent, or Firm*—Sughrue Mion, PLLC

(57) ABSTRACT

Described is a structural body including at least partially an aluminum member having on a surface an anodized film with micropores present, in which: the micropores have a coefficient of variation in pore size of 5 to 50%; and the micropores are each sealed with a metal. The structural body can generate localized plasmon resonance having a sufficiently large intensity and be produced at low cost through a simple production process, and having a large surface area.

13 Claims, 3 Drawing Sheets

OTHER PUBLICATIONS

H. Masuda et al., "Fabrication of Gold Nanodot Array Using Anodic Porous Alumina as an Evaporation Mask" Japanese Journal of Applied Physics, vol. 35, Jan. 15, 1996, p. 126-129.

H. Masuda et al., "Hoghly Ordered Nanochannel-Array Architecture in Anodic Alumina" American Institute of Physics, vol. 71, No. 19, Nov. 10, 1997, p. 2770-2772.

Masuda H. et al., "Spatially selective Metal Deposition into a Hole-Array Structure of Anodic Porous Alumina Using a Microelectrode"; Japanese Journal of Applied Physics, Japan Society of Applied Physics, Tokyo, JP.; vol. 37 No. 9A/B, Part 2, Sep. 15, 1998; pp. L1090-L1092, XP001180746 ISSN:0021-4922.

Yuldashev S U et al., "Growth of ZNO Nanowires by Electrochemical Deposition Into Porous Alumina on Silicon Substrates"; Journal of the Korean Physical Society, Seoul KR.; vol. 42, Feb. 2003, pp. S216-S218; XP008037658; ISSN: 0374-4884.

* cited by examiner

FINE STRUCTURAL BODY AND METHOD OF PRODUCING THE SAME

The entire contents of literatures cited in this specification are incorporated by reference.

BACKGROUND OF THE INVENTION

The present invention relates to a structural body (fine structural body) employing an aluminum member having on a surface an anodized film with micropores present, and to a method of producing the same.

In technical fields of thin films, thin wires, dots, and the like of metals or semiconductors, an electrically, optically, or chemically specific phenomenon is known to occur due to confinement of motions of free electrons in the metals or semiconductors each having a size smaller than a certain characteristic length. Such a phenomenon is referred to as "quantum-mechanical size effect (quantum size effect)". Research and development of functional materials applying such a specific phenomenon have been currently conducted actively. To be specific, a material having a fine structure of less than several hundred nm is referred to as a "fine structural body" or a "nanostructural body", and is regarded as one of the targets for material development.

An example of a method of producing such a fine structural body includes a method of directly producing a nanostructural body through a semiconductor processing technique including a fine pattern formation technique such as photolithography, electron beam exposure, or X-ray exposure.

Of those, researches on a method of producing a nanostructural body having an ordered fine structure have received attention, and have been conducted extensively.

An example of a method of forming a self-regulated, ordered structure involves subjecting aluminum to anodizing treatment in an electrolyte, to thereby obtain an anodized alumina film (anodized film). The anodized film is known to have ordered fine pores (micropores) each having a pore size of about several nm to about several hundred nm. A perfectly ordered arrangement may be obtained utilizing self-ordering property of the anodized film. The perfectly ordered arrangement theoretically has cells of hexagonal prisms each having a base of an equilateral hexagon formed around a micropore as a center. Lines connecting adjacent micropores are known to form equilateral triangles.

For example, H. Masuda et al., Jpn. J. Appl. Phys., Vol. 37 (1998), pp. L1340-1342, Part 2, No. 11A, 1 Nov. 1998 (FIG. 2) describes an anodized film having variation in pore size of micropores within 3%. Further, "Surface Finishing Handbook", edited by The Surface Finishing Society of Japan (1998), The Nikkan Kogyo Shimbun, Ltd., pp. 490-553 describes natural formation of pores on an anodized film in the course of oxidation. Further, Hideki Masuda, "Highly ordered metal nanohole arrays based on anodized alumina", Solid State Physics, 1996, Vol. 31, No. 5, pp. 493-499 proposes formation of an Au dot array on an Si substrate using a porous oxide film as a mask.

The greatest characteristic of the anodized film as a material is that micropores are arranged parallel at substantially equal intervals in a direction substantially vertical with respect to a surface of a substrate to take a honeycomb structure. An additional characteristic thereof is that a pore diameter, a distance between pores, and a pore depth of the micropores can be controlled relatively freely unlike those of other materials (see Hideki Masuda, "Highly ordered metal nanohole arrays based on anodized alumina" (supra).

Application examples of the anodized film include various devices such as a nanodevice, a magnetic device, and a phosphor. For example, JP 2000-31462 A (the term "JP XX-XXXXXX A" as used herein means an "unexamined published Japanese patent application") describes application examples thereof including: a magnetic device having micropores filled with Co or Ni as a magnetic metal; a magnetic device having micropores filled with ZnO as a phosphor; and a biosensor having micropores filled with an enzyme/antibody.

Further, in a field of biosensing, JP 2003-268592 A describes an example of a structure having micropores of an anodized film filled with a metal as a sample holder for Raman spectroscopic analysis.

Raman scattering refers to scattering of incident light (photon) caused by collision of the incident light with a particle, which induces inelastic collision with a particle and change in energy. Raman scattering is used as a technique for spectroscopic analysis, but the scattering light for measurement must have an enhanced intensity for improvement of sensitivity and precision of analysis.

A surface-enhanced resonance Raman scattering (SERRS) phenomenon is known as a phenomenon for enhancing Raman scattered light. The phenomenon further enhances scattering of light by molecules of certain species adsorbed on a surface of a metal electrode, a sol, a crystal, a deposited film, a semiconductor, or the like compared to scattering in a solution. A significant enhancing effect of $10^{11}$ to $10^{14}$ times may be observed on gold or silver, in particular. A mechanism for causing the SERRS phenomenon is not yet clarified, but surface plasmon resonance presumably has an effect thereon. JP 2003-268592 A also aims at utilizing the principle of plasmon resonance as means for enhancing the Raman scattering intensity.

Plasmon resonance refers to a phenomenon causing interaction of a plasmon wave, which is a localized electron density wave, with an electromagnetic wave (resonance excitation) to form a resonance state when a surface of a noble metal such as gold or silver is irradiated with light and the surface of the metal is brought into an excited state. Particularly, surface plasmon resonance (SPR) refers to a phenomenon causing collective vibrations of free electrons when a surface of a metal is irradiated with light and the free electrons on the metal surface are brought into excited states. Further, the surface plasmon resonance causes surface plasmon waves to generate strong electric field.

An electric field is enhanced by several orders ($10^8$ to $10^{10}$ times, for example) in a region in the vicinity of a surface where plasmon resonance takes place, more specifically, in a region within about 200 nm from the surface, and significant enhancement in various optical effects are observed. For example, when light enters a prism having a thin film of gold or the like deposited at an angle of a critical angle or more, a change in dielectric constant of a surface of the thin film can be detected with high sensitivity as a change in intensity of reflected light due to the surface plasmon resonance phenomenon.

To be specific, use of an SPR apparatus applying the surface plasmon resonance phenomenon allows measurement of a reaction amount or bonding amount between biomolecules, or kinetic analysis without labeling and at real-time. The SPR apparatus is applied to researches on immune response, signal transduction, or interaction between various substances such as proteins and nucleic acids. Recently, a paper describing analysis of a trace amount of dioxins using an SPR apparatus has also been reported (see I. Karube et al., Analytica Chimica Acta, 2001, Vol. 434, No. 2, pp. 223-230).

Various methods for enhancing plasmon resonance have been studied, and a technique of localizing plasmon by forming a metal into isolated particles, not into a thin film is known. For example, JP 2003-268592 A describes a technique of localizing plasmon by providing metal particles in pores of an ordered anodized film.

A research report describes that when localized plasmon resonance of metal particles is utilized, the metal particles locating close to one another enhances an intensity of an electric field at a gap between the metal particles, thereby realizing a state where plasmon resonance occurs more easily (see Takayuki Okamoto, "Researches on interaction of metal nanoparticles and on biosensors", on-line, URL: http://www.plasmon.jp/reports/okamoto.pdf, searched on Nov. 27, 2003). That is, locating metal particles close to one another becomes a critical requirement in a device employing localized plasmon resonance. For example, it is important that the metal particles be located close to one another within a distance of 200 nm without being in contact with each other.

SUMMARY OF THE INVENTION

The inventors of the present invention have conducted intensive studies on a device employing localized plasmon resonance, and have found that a device employing a conventional self-ordered anodized film has a problem in that the resonance intensity is not sufficiently large.

Further, the conventional self-ordered anodized film must be produced under strictly controlled conditions, and must be subjected to anodizing treatment for a long period of time. Thus, the conventional self-ordered anodized film has a problem in that the film is hardly put into practical use industrially from the viewpoints of cost and treatment on a large surface area.

An object of the present invention is therefore to provide a structural body capable of generating localized plasmon resonance having a sufficiently large intensity, capable of being produced at low cost through a simple production process, and having a large surface area.

The inventors of the present invention have further conducted intensive studies and have found that it is difficult to locate metal particles sufficiently close to one another when pores are filled with the metal particles through electrodeposition in an anodized film having a uniform pore size and formed through a conventional self-ordering anodizing treatment.

That is, when micropores are filled with the metal particles through electrodeposition, precipitation begins selectively from inside of the micropores having high electrical conductivity. As the precipitation progresses, a precipitate protrudes from the opening of each micropore to form metal particles, which are exposed on the anodized film.

The anodized film having a uniform pore size has a large distance among all metal particles when the amount of electrodeposition is small. In contrast, all metal particles are brought into contact with one another when the amount of electrodeposition is large. Thus, it is difficult to control the distance between the metal particles to a sufficiently short distance for easily generating plasmon resonance by adjusting the amount of electrodeposition.

Further, in a method using a dispersion liquid of metal colloid particles, a particle size of the metal colloid particles to be used varies. Thus, the inventors of the present invention have found that it is difficult to locate the metal particles efficiently and sufficiently close to one another in an anodized film having a uniform pore size.

Meanwhile, the inventors of the present invention have found that ordering property of the pore arrangement of the anodized film is not necessarily required strictly depending on types of actual industrial applications, and slight reduction in ordering property may be allowed in the application of the localized plasmon resonance. Further, the inventors of the present invention have found that there is a correlation between variation in pore size and the ordering property of the pore arrangement, and that the ordering property of the pore arrangement can be controlled while the pore size distribution is controlled.

Based on those findings, the inventors of the present invention have attained a structural body of the present invention capable of generating localized plasmon resonance having a sufficiently large intensity, capable of being produced at low cost through a simple process, and having a large area by controlling the variation in pore size of micropores into a coefficient of variation within a specific range.

That is, the present invention provides the following items (1) to (15).

(1) A structural body including at least partially an aluminum member having on a surface an anodized film with micropores present, in which: the micropores have a coefficient of variation in pore size of 5 to 50%; and the micropores are each sealed with a metal.

(2) The structural body according to the above item (1), in which: the anodized film has a thickness of 0.1 to 1 µm; the micropores have an average pore size of 0.01 to 0.5 µm and an average pore density of 50 to 150 pores/µm$^2$; the micropores collectively account for an area ratio of 20 to 50%; and the structural body has a surface porosity of 20% or less.

(3) The structural body according to the above item (1) or (2), in which a surface of the anodized film has a surface property selected from hydrophilic property and hydrophobic property.

(4) The structural body according to any one of the above items (1) to (3), in which the metal is one of a single particle and an aggregate and is produced through one of an electrodeposition method and a method involving applying a dispersion liquid of metal particles and drying the applied liquid.

(5) The structural body according to any one of the above items (1) to (4), in which the aluminum member has an aluminum purity of 99.5 wt % or more.

(6) The structural body according to any one of the above items (1) to (5), in which the metal is one of gold and silver.

(7) The structural body according to any one of the above items (1) to (5), in which the metal is a magnetic metal.

(8) The structural body according to the above item (7), in which the magnetic metal is one of a single substance and an alloy of at least one element selected from the group consisting of Fe, Co, and Ni.

(9) A method of producing the structural body according to any one of the above items (1) to (8), including the steps of: forming pits on a surface of the aluminum member; subjecting the aluminum member to anodizing treatment for forming the anodized film having the micropores at positions of the pits; and filling the metal into the micropores for sealing.

(10) The method of producing a structural body according to the above item (9), in which the step of forming pits on a surface of the aluminum member is conducted through anodizing treatment.

(11) The method of producing a structural body according to the above item (10), in which, in the step of forming pits on a surface of the aluminum member, the anodized film formed through the anodizing treatment has a thickness of 10 to 50 µm.

(12) A sample holder for Raman spectroscopic analysis employing the structural body according to any one of the above items (1) to (8).

(13) A magnetic recording medium employing the structural body according to the above item (7) or (8).

(14) A method of producing the structural body according to any one of the above items (1) to (8), including: an anodizing treatment step by subjecting a surface of the aluminum member to anodizing treatment for forming an anodized film with micropores present; a surface treatment step by subjecting a surface of the anodized film to a surface treatment selected from hydrophilic treatment and hydrophobic treatment after the anodizing treatment step for imparting a surface property; and a sealing treatment step for sealing the micropores with a metal after the surface treatment step.

(15) A method of producing the structural body according to any one of the above items (1) to (8), including: an anodizing treatment step by subjecting a surface of the aluminum member to anodizing treatment using an electrolyte containing one treatment agent of a hydrophilic agent and a hydrophobic agent for forming an anodized film having micropores present and a surface property; and a sealing treatment step for sealing the micropores with a metal after the anodizing treatment step.

A sample holder for Raman spectroscopic analysis employing the structural body of the present invention provides very high sensitivity because the metal particles are located close to one another to enhance localized plasmon resonance.

Further, the structural body of the present invention can be suitably used for other devices each employing plasmon resonance.

Further, the structural body of the present invention can be produced through a simple process in a short period of time at low cost even if the structural body has a large area.

DETAILED DESCRIPTION OF THE INVENTION

Figure 1:
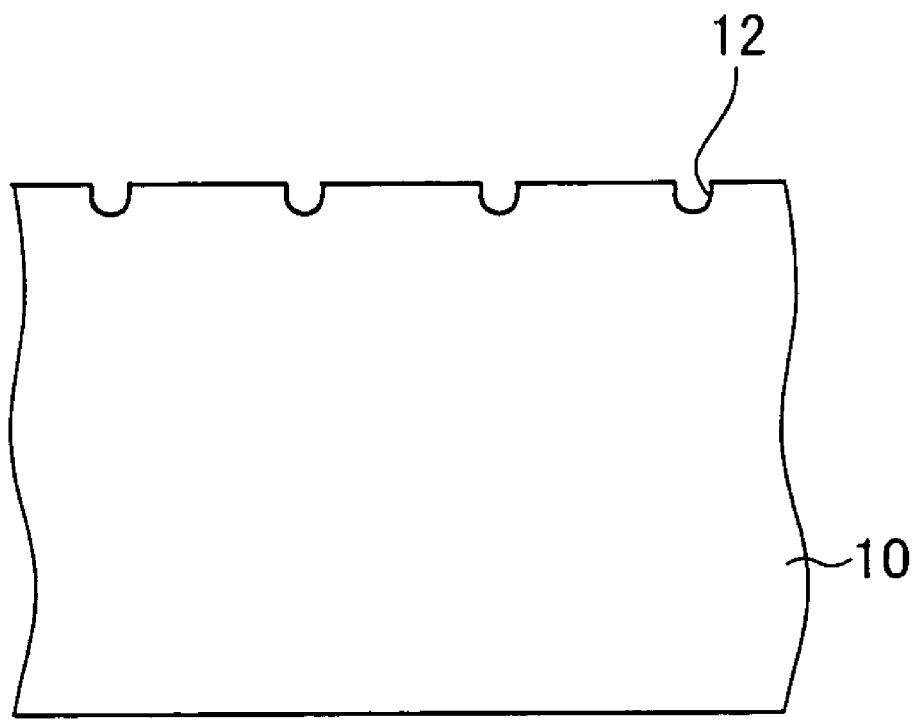
FIG. 1 is a schematic sectional view showing an aluminum member having pits formed on a surface, used for a structural body of the present invention.

Hereinafter, the present invention will be described in more detail.

<Aluminum Member>

At least a part of a structural body of the present invention includes an aluminum member having on a surface an anodized film with micropores present.

The aluminum member having on a surface an anodized film used in the present invention can be obtained by subjecting a surface of a member having an aluminum surface to anodizing treatment.

A member having an aluminum surface is not particularly limited, and examples thereof include: aluminum substrates such as a high purity aluminum substrate having a purity of 99.9% or more and a substrate prepared through deposition of high purity aluminum having a purity of 99.9% or more on low purity aluminum (recycled material, for example); a substrate coated with high purity aluminum through a method of deposition or sputtering on a surface of a silicon wafer, quartz, or glass; and a resin substrate prepared by laminating aluminum.

A substrate having an aluminum foil laminated thereon may be obtained by providing an aluminum foil on a substrate such as a resin substrate through an adhesive layer using an adhesive.

Various specific examples of the adhesive include: aromatic polyether-based one component moisture curing adhesives (such as SF102RA, available from Dainippon Ink and Chemicals, Inc.); aromatic polyether-based two component curing adhesives (such as 2K-SF-302A/HA550B, available from Dainippon Ink and Chemicals, Inc.); aliphatic polyester-based two component curing adhesives (such as 2K-SF-250A/HA280, available from Dainippon Ink and Chemicals, Inc.); aqueous dry laminating adhesives (such as WS305A/LB-60, WS201A/LB-60, WS325A/LJ-55, WS350A/LA-100, and WS-320A, all available from Dainippon Ink and Chemicals, Inc.); organic solvent type dry laminating adhesives (such as LX-747A/KX-75, LX-88H(T)/KW-75, and LX-732/KRX-90, all available from Dainippon Ink and Chemicals, Inc.); epoxy-based one component heat curing adhesives (EP106, EP138, EP160, EP170, and EP171, all available from Cemedine Co., Ltd.); one component anaerobic curing adhesives such as an acrylic oligomer (SGA) (such as Y-800 series, Y-805 GH, all available from Cemedine Co., Ltd.); special silicone-modified polymer-based one component elastic adhesives (such as Super X, available from Cemedine Co., Ltd.); phenol resin composite polymer-based adhesives (such as: a mixture of a phenol resin, and butadiene or acrylonitrile rubber; various mixtures of a phenol resin, and polyvinyl acetate, polyvinyl acetal, polyvinyl butyral, or polyvinyl formal; and a mixture of a phenol resin and epoxy); two component condensation reaction type adhesives; two component addition reaction type adhesives such as epoxy and isocyanate; two component radical polymerization type adhesives such as acrylic oligomer (SGA) and the like; heat melting adhesives such as polyimide, polyester, and polyolefin; pressure sensitive adhesives such as rubber and polyacrylate; one component normal temperature curing adhesives each containing 2-cyanoacrylate as a main component; methyl 2-cyanoacrylate-based adhesives; ethyl 2-cyanoacrylate-based adhesives (such as Aron Alpha, available from Toagosei Co., Ltd.); and α-cyanoacrylate-based adhesives (such as 3000DX series, available from Cemedine Co., Ltd.).

The adhesive layer has a thickness of preferably 3 to 50 μm, more preferably 5 to 20 μm, furthermore preferably 10 to 20 μm. The thickness of the adhesive layer can be determined through a method of observing a broken surface with an SEM (scanning electron microscope), for example.

An aluminum foil is provided on the adhesive layer. The aluminum foil has a thickness of preferably 1 to 10 μm, more preferably 1 to 5 μm, and furthermore preferably 2 to 4 μm.

As described below, formation of pits as starting points for the anodizing treatment through a self-ordering method requires a member having an aluminum surface to have a certain thickness, and thus an aluminum substrate is preferable.

Of the aluminum members, a surface provided with an anodized film through anodizing treatment has an aluminum purity of preferably 99.5 wt % or more, more preferably 99.80 wt % or more, and preferably less than 99.99 wt %, more preferably 99.95 wt % or less. An aluminum purity of 99.5 wt % or more allows a sufficiently ordered pore arrangement, and an aluminum purity of less than 99.99 wt % allows production at low cost.

The surface of the aluminum member is preferably subjected to degreasing treatment and mirror finish treatment in advance.

<Degreasing Treatment>

The degreasing treatment is conducted for removal of an organic component (mainly oil component) or the like adhered to the surface of an aluminum member through dissolution using an acid, an alkali, an organic solvent, or the like. A conventionally known degreasing agent may be used for the degreasing treatment.

To be specific, various commercially available degreasing agents may be used through a predetermined method, for example.

Further, the degreasing treatment can be conducted by immersing an aluminum member in an aqueous solution of sodium hydroxide at a pH of 10 to 13 and a temperature from about 30 to 50° C., or in an aqueous solution of sulfuric acid at a pH of 1 to 4 and a temperature from about 40 to 70° C., for example, for a period of time required for slightly generating air bubbles from the aluminum surface.

A preferable example of the degreasing treatment includes a method involving: washing an aluminum member with acetone; and immersing the washed aluminum member in sulfuric acid at a pH of 4 and a temperature of 50° C. This method is preferable because the oil component on the aluminum surface is removed while dissolution of aluminum hardly takes place.

Of those, the following methods are preferable.

Examples thereof include: a method involving bringing organic solvents such as various alcohols, various ketones, benzine, and volatile oil into contact with an aluminum surface at normal temperature (organic solvent method); a method involving bringing a liquid containing a surfactant such as soap or neutral detergent into contact with an aluminum surface at a temperature from normal temperature to 80° C. and then washing the aluminum surface with water (surfactant method); a method involving bringing an aqueous solution of sulfuric acid in a concentration of 10 to 200 g/L into contact with an aluminum surface at a temperature from normal temperature to 70° C. for 30 to 80 sec and then washing the aluminum surface with water; a method involving bringing an aqueous solution of sodium hydroxide in a concentration of 5 to 20 g/L into contact with an aluminum surface at normal temperature for about 30 sec, and at the same time passing a direct current at a current density of 1 to 10 A/dm$^2$ with the aluminum surface as a cathode for electrolysis, and then bringing an aqueous solution of nitric acid in a concentration of 100 to 500 g/L into contact with the aluminum surface for neutralization; a method involving bringing various known electrolytes for anodizing treatment into contact with an aluminum surface at normal temperature, and at the same time passing a direct current or alternating current at a current density of 1 to 10 A/dm$^2$ with the aluminum surface as a cathode for electrolysis; a method involving bringing an aqueous alkali solution in a concentration of 10 to 200 g/L into contact with an aluminum surface at 40 to 50° C. for 15 to 60 sec and then bringing an aqueous solution of nitric acid in a concentration of 100 to 500 g/L into contact with the aluminum surface for neutralization; a method involving bringing an emulsified liquid prepared by mixing a surfactant, water, or the like into light oil, kerosene, or the like into contact with an aluminum surface at a temperature from normal temperature to 50° C. and then washing the aluminum surface with water (emulsification degreasing method); and a method involving bringing a mixed liquid of sodium carbonate, phosphates, a surfactant, and the like into contact with an aluminum surface at a temperature from normal temperature to 50° C. for 30 to 180 sec and then washing the aluminum surface with water (phosphate method).

The degreasing treatment is preferably a method which can remove the oil component on the aluminum surface and which hardly causes dissolution of aluminum. From such viewpoints, the organic solvent method, the surfactant method, the emulsification degreasing method, and the phosphate method are preferable.

<Mirror Finish Treatment>

The mirror finish treatment is conducted for elimination of surface unevenness of an aluminum member and for improvement of uniformity or reproducibility of sealing treatment through electrodeposition or the like. An example of the surface unevenness of the aluminum member includes a rolling line generated during rolling of an aluminum member produced through rolling.

In the present invention, the mirror finish treatment is not particularly limited, and a conventionally known method can be used. Examples thereof include mechanical polishing, chemical polishing, and electrolytic polishing.

Examples of the mechanical polishing include: a method involving polishing with various commercially available polishing cloths; and a method in which various commercially available abrasives (such as diamond and alumina) are used in combination with buffing. A specific preferable example thereof includes a method in which abrasives are used while changing the particle size with time from coarser one to finer one. In this case, an abrasive to be used finally is preferably #1500. The mechanical polishing can provide a glossiness of 50% or more (50% or more in a rolling direction and in a width direction for rolled aluminum).

Examples of the chemical polishing include various methods described in "Aluminum Handbook", 6th edition, Japan Aluminum Association, 2001, pp. 164-165.

Further examples thereof include: a phosphoric acid-nitric acid method; Alupol I; Alupol V; Alcoa R5; an $H_3PO_4$—$CH_3COOH$—Cu method; and an $H_3PO_4$—$HNO_3$—$CH_3COOH$ method. Of those, a phosphoric acid-nitric acid method, an $H_3PO_4$—$CH_3COOH$—Cu method, and an $H_3PO_4$—$HNO_3$—$CH_3COOH$ method are preferable.

The chemical polishing can provide a glossiness of 70% or more (70% or more in a rolling direction and in a width direction for rolled aluminum).

Examples of the electrolytic polishing include various methods described in "Aluminum Handbook", 6th edition, Japan Aluminum Association, 2001, pp. 164-165.

A preferable example thereof includes a method described in U.S. Pat. No. 2,708,655.

Another preferable example thereof includes a method described in "Jitsumu Hyomen Gijutsu", Vol. 33, No. 3, 1986, pp. 32-38.

The electrolytic polishing can provide a glossiness of 70% or more (70% or more in a rolling direction and in a width direction for rolled aluminum).

Those methods can be arbitrarily combined and used. For example, the method in which abrasives are used while changing the particle size with time from coarser one to finer one, is followed by the electrolytic polishing method.

The mirror finish treatment can provide a surface having an average surface roughness $R_a$ of 0.1 μm or less and a glossiness of 50% or more. The average surface roughness $R_a$ is preferably 0.03 μm or less, more preferably 0.02 μm or less. The glossiness is preferably 70% or more, more preferably 80% or more.

The glossiness refers to a regular reflectance determined in accordance with JIS Z 8741-1997 "Method 3, 60° mirror gloss" in a direction perpendicular to a rolling direction. To be specific, the glossiness is measured using a glossmeter (such as VG-1D, manufactured by Nippon Denshoku Industries Co., Ltd.) at an incident and reflected angle of 60° when a regular reflectance is 70% or less and at an incident and reflected angle of 20° when a regular reflectance exceeds 70%.

<Pit Formation>

A method of subjecting a surface of a member having an aluminum surface to anodizing treatment preferably includes a method of forming pits serving as starting points for micropore formation in the anodizing treatment before the anodizing treatment for formation of micropores (hereinafter, may also be referred to as "the anodizing treatment"). Such formation of pits facilitates control of the arrangement of micropores and variation in pore size within a desired range.

A method of forming pits is not particularly limited. Examples thereof include: a self-ordering method utilizing self-ordering property of an anodized film (anodizing treatment); a physical method; a particle beam method; a block copolymer method; and a resist interference exposure method.

<Self-Ordering Method>

The self-ordering method is a method for improving ordering property by utilizing property of micropores of an anodized film to be arranged orderly and by removing factors disturbing an ordered arrangement. To be specific, the self-ordering method involves: using high purity aluminum; forming an anodized film thereon at low speed and at a voltage adequate for the type of electrolyte used over a long period of time (such as several hours to less than 20 hours); and subjecting aluminum to film removal treatment.

In this method, the pore size depends on the voltage, and thus a desired pore size can be obtained to some extent by controlling the voltage.

Representative examples of the self-ordering method include methods described in: J. Electrochem. Soc., Vol. 144, No. 5, May 1997, p. L128; Jpn. J. Appl. Phys., Vol. 35 (1996), Part 2, No. 1B, p. L126; Appl. Phys. Lett., Vol. 71, No. 19, 10 November 1997, p. 2771; and H. Masuda et al., Jpn. J. Appl. Phys. (supra).

The methods described in the documents have technical characteristics in that each method involves using a high purity material and subjecting the material to treatment at a specific voltage adequate for the electrolyte used, at a relatively low temperature, and for a long period of time. To be specific, each method involves using a material having an aluminum purity of 99.99 wt % or more, and a self-ordering method is conducted under the following conditions.

0.3 mol/L sulfuric acid, 0° C., 27 V, 450 min (J. Electrochem. Soc. (supra))

0.3 mol/L sulfuric acid, 10° C., 25 V, 750 min (J. Electrochem. Soc. (supra))

0.3 mol/L oxalic acid, 17° C., 40-60 V, 600 min (Jpn. J. Appl. Phys. (supra))

0.04 mol/L oxalic acid, 3° C., 80 V, film thickness of 3 μm (Appl. Phys. Lett. (supra))

0.3 mol/L phosphoric acid, 0° C., 195 V, 960 min (Appl. Phys. Lett. (supra))

In each of the methods described in the documents, the film removal treatment for removing the anodized film through dissolution using an aqueous mixed solution of chromic acid and phosphoric acid at about 50° C. takes 12 or more hours. Treatment using a boiled aqueous solution destroys and disturbs the starting points for ordering, and thus, a mixed aqueous solution is used without boiling.

The self-ordered anodized film has higher ordering property in a portion closer to the aluminum member. The film is removed once and a base portion of the anodized film remained on the aluminum member is exposed on the surface, to thereby obtain ordered pits. Thus, in the film removal treatment, aluminum is not dissolved, and the anodized film alone, which is aluminum oxide, is dissolved.

As a result, in the methods described in the documents, variation (coefficient of variation) in pore size is 3% or less although the pore sizes of micropores differ from each other.

The self-ordering anodizing treatment used in the present invention may employ a method involving applying electric power to an aluminum member as an anode in a solution having an acid concentration of 1 to 10 wt %. Examples of the solution used for the anodizing treatment include sulfuric acid, phosphoric acid, chromic acid, oxalic acid, sulfamic acid, benzenesulfonic acid, and amidosulfonic acid. The solution may be used alone, or may be used as a mixture of two or more thereof.

The conditions for the self-ordering anodizing treatment cannot be determined generally because the conditions vary in accordance with an electrolyte to be used. However, appropriate conditions generally include: an electrolyte concentration of 1 to 10 wt %; a liquid temperature of 0 to 20° C.; a current density of 0.1 to 10 A/dm$^2$; a voltage of 10 to 200 V; and an electrolysis time of 2 to 20 hours.

The self-ordered anodized film has a thickness of preferably 5 to 100 μm, more preferably 10 to 50 μm.

In the present invention, the self-ordering anodizing treatment is conducted for preferably 1 to 16 hours, more preferably 2 to 12 hours, and furthermore preferably 2 to 7 hours.

The film removal treatment is conducted for preferably 0.5 to 10 hours, more preferably 2 to 10 hours, and furthermore preferably 4 to 10 hours.

The self-ordering anodizing treatment and the film removal treatment are each conducted for a shorter period of time than those of the known methods. Thus, the ordering property of the micropore arrangement deteriorates slightly and the variation in pore size increases relatively to a coefficient of variation in a range of 5 to 50%.

As described above, the anodized film is formed through a self-ordering method, and the film is dissolved and removed. Further, the anodizing treatment described below is conducted again under the same conditions to thereby obtain substantially straight micropores formed substantially perpendicularly to the surface of the film.

<Physical Method>

An example of the physical method includes a method employing press patterning. A specific example thereof includes a method involving forming pits by pressing a substrate having protrusions on a surface against an aluminum surface. A method described in JP 10-121292 A can be used, for example.

Further, another method of forming pits involves: densely arranging polystyrene spheres on an aluminum surface; depositing $SiO_2$ thereon; removing the polystyrene spheres; and etching a substrate using the deposited $SiO_2$ as a mask.

<Particle Beam Method>

The particle beam method is a method of forming pits by irradiating an aluminum surface with a particle beam. The particle beam method has an advantage in that positions of the pits may be adjusted freely.

Examples of the particle beam include a charged particle beam, a focused ion beam (FIB), and an electron beam.

The particle beam method can disturb the ordering property of positions of the pits using a random number for determination of the positions of the pits. Thus, the order of arrangement of micropores formed through the anodizing treatment to be described below is disturbed, to thereby realize desired variation in pore size.

The positions of the pits can be set at desired positions using the following equation.

(Coordinates of desired position)=(Coordinates of perfectly ordered position)±(Coordinates of perfectly ordered position)×(Coefficient of variation)×(Random number)

When sealing treatment is conducted through an electrodeposition method, a coefficient of variation in pore size is preferably 0.05 to 0.5, more preferably 0.07 to 0.3, and furthermore preferably 0.1 to 0.2.

When the sealing treatment is conducted through a method using metal colloid particles, a coefficient of variation in pore size is determined in accordance with a particle size distribution of the metal colloid particles used.

The particle beam method may employ a method described in JP 2001-105400 A, for example.

<Block Copolymer Method>

The block copolymer method is a method of forming pits involving: forming a block copolymer layer on an aluminum surface; forming a sea-island structure on the block copolymer layer through heat annealing; and removing an island portion.

The block copolymer method may employ a method described in JP 2003-129288 A, for example.

<Resist Interference Exposure Method>

The resist interference exposure method is a method involving: providing a resist on an aluminum surface; exposing or developing the resist; and forming pits on the resist which penetrate to the aluminum surface.

The resist interference exposure method may employ a method described in JP 2000-315785 A, for example.

Of the various methods of forming pits, the self-ordering method, the FIB method, and the resist interference exposure method are desirable from the viewpoints of allowing uniform formation of pits across a large area of about 10 cm-square or more.

In consideration of a production cost, the self-ordering method is most preferable. The FIB method is also preferable from the viewpoint of freely controlling the arrangement of micropores.

The pits to be formed each have a depth of preferably about 10 nm or more. Further, the distance between centers of the pits is preferably equal to or less than the desired pore size.

FIG. 1 is a schematic sectional view showing an aluminum member having pits formed on a surface, used for a structural body of the present invention.

As shown in FIG. 1, an aluminum member 10 has pits 12 on its surface.

<The Anodizing Treatment>

As described above, an anodized film is formed through the anodizing treatment preferably after formation of pits on an aluminum surface.

As a preferable mode of the present invention, the surface of the obtained anodized film has a surface property selected from hydrophilic property and hydrophobic property. A method of imparting one of the surface properties to the surface of the anodized film is not particularly limited. Examples thereof include: a method involving forming an anodized film, and subjecting the surface to hydrophilic treatment or hydrophobic treatment to impart the corresponding surface property; and a method involving subjecting the surface to anodizing treatment using an electrolyte containing a hydrophilic agent or a hydrophobic agent, and forming the anodized film.

The anodizing treatment may employ a conventionally known method, and is preferably conducted under the same conditions as those of the self-ordering method as described above. The same applies to the case where the anodized film is formed and then the surface thereof is subjected to hydrophilic treatment or hydrophobic treatment.

Further examples of the anodizing treatment include: a method involving intermittently repeating switching of current on and off while a constant direct voltage is applied; and a method involving repeatedly switching current on and off while a direct voltage is intermittently changed. Those methods are preferable because fine micropores are formed on the anodized film and uniformity is improved particularly in sealing treatment through electrodeposition.

In the method involving intermittently changing the voltage as described above, the voltage is preferably reduced sequentially. In this way, the resistance of the anodized film can be reduced, and the uniformity is achieved in the subsequent electrodeposition.

When the anodizing treatment is conducted at low temperatures, micropores are arranged in an ordered manner and has a uniform pore size.

In the present invention, the anodizing treatment is conducted at relatively high temperatures, to thereby easily disturb the arrangement of micropores and facilitate control of variation in pore size within a predetermined range. The variation in pore size can be controlled by treatment time as well.

The anodized film has a thickness of preferably 0.5 to 10 times, more preferably 1 to 8 times, furthermore preferably 1 to 5 times the pore size for easy sealing.

The pore size is preferably 10 nm or more if electrodeposition treatment is conducted later as the sealing treatment.

Thus, a preferable mode of the anodized film includes: a thickness of 0.1 to 1 μm; and an average pore size of micropores of 0.01 to 0.5 μm.

An average pore density is preferably 50 to 1,500 pores/μm².

The micropores preferably account for an area ratio of 20 to 50%.

The area ratio accounted for by the micropores is a ratio of a total area of openings of micropores to an area of the aluminum surface. In calculation of the area ratio accounted for by the micropores, micropores include micropores sealed or not sealed with a metal. To be specific, the area ratio accounted for by the micropores is determined by measuring a surface porosity before the sealing treatment.

When the anodizing treatment is conducted using an electrolyte containing a treatment agent, the anodizing treatment can be conducted in the same manner as the methods described above except that the electrolyte contains a hydrophilic agent or a hydrophobic agent as a treatment agent.

Examples of the hydrophilic agent include hydrophilic inorganic fine particles and a water-soluble resin.

Specific examples of the hydrophilic inorganic fine particles include: colloidal silica (such as SNOWTEX ST-O, available from Nissan Chemical Industries, Ltd., $SiO_2$ content of 20 wt %, particle size of 10 to 20 nm, pH of 2.0 to 4.0); and colloidal alumina (such as ALUMINASOL 500, available from Nissan Chemical Industries, Ltd., $Al_2O_3$ content of 20 wt %, $NO_3$ content of 1 wt % or less, boehmite sheet crystals, stabilized by nitric acid; ALUMINASOL 200, available from Nissan Chemical Industries, Ltd., $Al_2O_3$ content of 10 wt %, $CH_3COOH$ content of 3.5 wt % or less, feather-like, stabilized by acetic acid; and ALUMINASOL 100, available from Nissan Chemical Industries, Ltd., $Al_2O_3$ content of 10 wt %, Cl content of 3 wt % or less, feather-like, stabilized by hydrochloric acid).

Specific examples of the water-soluble resin include polyvinyl alcohol (PVA) and polyacrylic acid (PAA). Those are reagents available from Kanto Kagaku.

The hydrophilic agent as a liquid preferably has a neutral pH or a pH hardly changing the pH of the electrolyte for preventing gelation. The hydrophilic agent as a solid preferably has a pH hardly changing the pH of the electrolyte.

Examples of the hydrophobic agent include: colloidal hydrophobic resins; neutral emulsion resins such as a modified-styrene/butadiene copolymer-based latex and a medium hardened styrene-based mixed latex (including Nipol LX438C, available from ZEON Corporation, average particle size of 150 nm, pH of 7; and Nipol LX430, available from ZEON Corporation, average particle size of 150 nm, pH of 7); and acidic emulsion resins such as a modified-styrene/butadiene copolymer-based latex (including Nipol LX407AS, available from ZEON Corporation, average particle size of 100 to 140 nm, pH of 5 to 6) and an acrylate-based latex (including Nipol LX816, available from ZEON Corporation).

Further, a so-called water repellent agent can be used as a hydrophobic agent. An example of the water repellent agent includes a compound represented by the following formula (1).

$$R^1-Si(R^2)_3 \quad (1)$$

In the formula, $R^1$ represents an alkyl group having 3 or more carbon atoms which may have a substituent. R may be linear, branched, or cyclic.

Examples of a linear alkyl group include a propyl group, a butyl group, a pentyl group, a hexyl group, a heptyl group, an octyl group, a nonyl group, and a decyl group. Examples of a branched alkyl group include an isopropyl group, an isobutyl group, an isopentyl group, an isohexyl group, an isoheptyl group, an isooctyl group, an isononyl group, and an isodecyl group. Examples of a cyclic alkyl group include a cyclopropyl group, a cyclobutyl group, a cyclopentyl group, a cyclohexyl group, a cycloheptyl group, a cyclooctyl group, a cyclononyl group, and a cyclodecyl group.

The alkyl group may have a substituent, and the substituent is not particularly limited. Examples of the substituent include a halogen atom, an alkyl group, an allyl group, an aryl group, an allylaryl group, and a group obtained by combining the above groups.

Examples of the halogen atom include fluorine, chlorine, bromine, and iodine. Examples of the alkyl group include a methyl group, an ethyl group, and the same alkyl groups exemplified for the above R.

Of those, the substituent is preferably fluorine.

The compound represented by the above formula (1) can increase hydrophobic property of the surface with increasing number of carbon atoms in $R^1$, or increasing number of fluorine atoms if the compound has a fluorine atom as a substituent.

$R^2$ each represents independently a methoxy group, an ethoxy group, or an isocyanate group.

Examples of the compound represented by the above formula (1) include alkyl trimethoxysilane, alkyl triethoxysilane, fluoroalkyl trimethoxysilane, fluoroalkyl triethoxysilane, alkyl triisocyanatesilane, and fluoroalkyl triisocyanatesilane.

Of those, preferable examples thereof include: fluoroalkylsilane (FAS) such as fluoroalkyl trimethoxysilane and fluoroalkyl triethoxysilane; and fluoroalkyl triisocyanatesilane, which are room temperature curing water repellent agents.

When a hydrophilic agent or a hydrophobic agent is included in an electrolyte used for anodizing treatment, the content thereof is preferably 1 to 30 wt %, more preferably 5 to 20 wt % with respect to the total amount of the electrolyte. The content within the above range allows uniform anodizing treatment without causing burning even with a high voltage for the anodizing treatment.

Figure 2A:
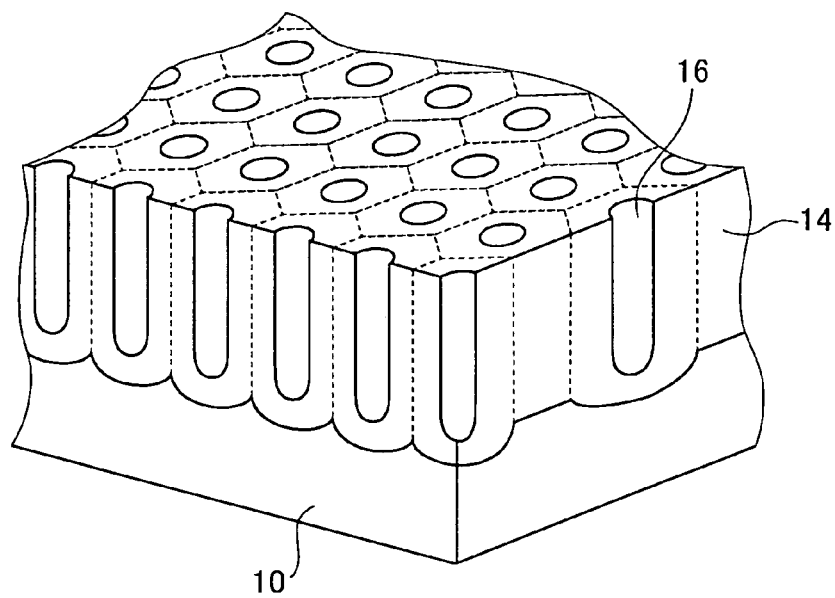
FIGS. 2A and 2B are each a schematic diagram showing an aluminum member having on a surface an anodized film with micropores present, used for a structural body of the present invention.
Figure 2B:
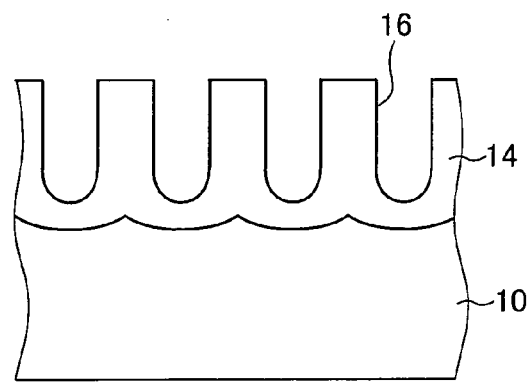

FIGS. 2A and 2B are each a schematic diagram showing an aluminum member having on a surface an anodized film with micropores present, used for a structural body of the present invention. FIG. 2A is a partially cut perspective view, and FIG. 2B is a sectional view.

As shown in FIGS. 2A and 2B, an aluminum member 10 has an anodized film 14 on its surface, and the anodized film 14 has micropores 16.

<Pore Widening Treatment>

The pore widening treatment refers to a treatment conducted after the anodizing treatment for enlarging the pore size of micropores by immersing an aluminum member in an aqueous acidic solution or an aqueous alkali solution and dissolving the anodized film.

In this way, the ordering property of the micropore arrangement and variation in pore size can be controlled easily. Further, a barrier film on the base portion of each micropore of the anodized film may be dissolved, to thereby allow selective electrodeposition inside the micropore and slight increase of variation in pore size.

When an aqueous acidic solution is used in the pore widening treatment, examples of the aqueous solution preferably used include: an aqueous solution of an inorganic acid such as sulfuric acid, phosphoric acid, nitric acid, or hydrochloric acid; and an aqueous solution of a mixture of the inorganic acids. The aqueous acidic solution preferably has a temperature of 25 to 40° C.

When an aqueous alkali solution is used in the pore widening treatment, an aqueous solution of at least one alkali selected from the group consisting of sodium hydroxide, potassium hydroxide, and lithium hydroxide is preferably used. The aqueous alkali solution preferably has a concentration of 0.1 to 5 wt %. The aqueous alkali solution preferably has a temperature of 25 to 35° C.

Specific examples of the aqueous acidic solution and the aqueous alkali solution preferably used include: a 50 g/L aqueous solution of phosphoric acid at 40° C.; a 0.5 g/L aqueous solution of sodium hydroxide at 30° C.; and a 0.5 g/L aqueous solution of potassium hydroxide at 30° C.

The immersion time in the aqueous acidic solution or the aqueous alkali solution is preferably 8 to 60 min, more preferably 10 to 50 min, and furthermore preferably 15 to 30 min.

<Other Treatments>

Further, other treatments can be conducted as required.

For example, when the surface property selected from hydrophilic property and hydrophobic property is imparted to the surface of the anodized film by subjecting the surface to the anodizing treatment using an electrolyte containing no treatment agent, the surface property selected from hydrophilic property and hydrophobic property is imparted to the surface by subjecting the surface of the anodized film to hydrophilic surface treatment or hydrophobic surface treatment after the anodizing treatment or after the subsequent pore widening treatment. Even when the surface is subjected to the anodizing treatment using an electrolyte containing a treatment agent, the surface treatment can be conducted thereafter.

A method for the hydrophilic treatment is not particularly limited. Examples thereof include: potassium fluorozirconate treatment described in U.S. Pat. No. 2,946,638; phosphomolybdate treatment described in U.S. Pat. No. 3,201,247; alkyltitanate treatment described in GB 1,108,559; polyacylic acid treatment described in DE 1,091,433; polyvinylphosphonic acid treatment described in DE 1,134,093 and GB 1,230,447; phosphonic acid treatment described in JP 44-6409 B (the term "JP XX-XXXXXX B" as used herein means an "examined Japanese patent publication"); phytic acid treatment described in U.S. Pat. No. 3,307,951; treatment by a salt of a lipophilic organic polymer compound and a divalent metal described in JP 58-16893 A and JP 58-18291 A; treatment involving providing a layer of hydrophilic cellulose (such as carboxymethylcellulose) containing a water-soluble metal salt (such as zinc acetate) described in U.S. Pat. No. 3,860,426; and treatment involving applying a water-soluble polymer having a sulfo group described in JP 59-101651 A.

Further examples thereof include treatments involving applications of: a phosphate described in JP 62-019494 A; a water-soluble epoxy compound described in JP 62-033692 A; a phosphoric acid-modified starch described in JP 62-097892 A; a diamine compound described in JP 63-056498 A; an inorganic acid or organic acid of amino acid described in JP 63-130391 A; an organic phosphonic acid having a carboxy group or hydroxy group described in JP 63-145092 A; a compound having an amino group and a phosphonic group described in JP 63-165183 A; a specific carboxylic acid derivative described in JP 2-316290 A; a phosphoric ester described in JP 3-215095 A; a compound having one amino group and one oxacid group of phosphor described in JP 3-261592 A; an aliphatic or aromatic phosphonic acid such as phenyl phosphonic acid described in JP 5-246171 A; a compound containing an S atom such as thiosalicylic acid described in JP 1-307745 A; and a compound having a group such as an oxacid of phosphor described in JP 4-282637 A.

Further examples of the method for the hydrophilic treatment include: a method involving immersing in an aqueous solution of alkali metal silicate such as sodium silicate or potassium silicate; and a method involving applying a hydrophilic vinyl polymer or a hydrophilic compound.

The hydrophilic treatment involving immersing in an aqueous solution of alkali metal silicate such as sodium silicate or potassium silicate can be conducted according to methods and procedures described in U.S. Pat. Nos. 2,714,066 and 3,181,461.

Examples of the alkali metal silicate include sodium silicate, potassium silicate, and lithium silicate. An aqueous solution of alkali metal silicate may contain sodium hydroxide, potassium hydroxide, lithium hydroxide, or the like in an appropriate amount.

The aqueous solution of alkali metal silicate may contain an alkali earth metal salt or a salt of a metal of Group 4 (Group IVA). Examples of the alkali earth metal salt include: nitrates such as calcium nitrate, strontium nitrate, magnesium nitrate, and barium nitrate; sulfates; hydrochlorides; phosphates; acetates; oxalates; and borates. Examples of the salt of the Group 4 (Group IVA) metal include titanium tetrachloride, titanium trichloride, potassium titanium fluoride, potassium titanium oxalate, titanium sulfate, titanium tetraiodide, zirconium chloride oxide, zirconium dioxide, zirconium oxychloride, and zirconium tetrachloride. The alkali earth metal salt or the salt of the Group 4 (Group IVA) metal may be used alone or as a mixture of two or more thereof.

Further, hydrophilic treatment through formation of a hydrophilic layer can be conducted according to the conditions and procedures described in JP 59-101651 A and JP 60-149491 A.

An example of a hydrophilic vinyl polymer used for the method includes a copolymer of a sulfo group-containing vinyl polymer compound such as polyvinyl sulfonic acid or p-styrenesulfonic acid having a sulfo group, and a normal vinyl polymer compound such as alkyl (meth)acrylate. An example of a hydrophilic compound used for the method includes a compound having at least one group selected from the group consisting of an —$NH_2$ group, a —COOH group, and a sulfo group.

Further, another method for the hydrophilic treatment involves: applying a liquid containing the above-described hydrophilic agent on the surface of the anodized film; and drying the liquid.

A method for the hydrophobic treatment is not particularly limited. An example of the method involves forming a hydrophobic layer using a compound including: carboxymethylcellulose; dextrin; gum arabic; organic phosphonic acids such as phosphonic acids each having an amino group (2-aminoethylphosphonic acid, for example), phenylphosphonic acid, naphthylphosphonic acid, alkylphosphonic acid, glycerophosphonic acid, methylendiphosphonic acid, and ethylenediphosphonic acid which may have a substituent; organic phosphoric acids such as phenylphosphoric acid, naphthylphosphoric acid, alkylphosphoric acid, and glycerophosphoric acid which may have a substituent; organic phosphinic acids such as phenylphosphinic acid, naphthylphosphinic acid, alkylphosphinic acid, and glycerophosphinic acid which may have a substituent; amino acids such as glycine and β-alanine; and amine hydrochlorides each having a hydroxy group such as triethanolamine hydrochloride. The compound may be used alone, or as a mixture of two or more thereof.

The hydrophobic layer may preferably employ a layer containing a polymer compound which has an acid group component and an onium group component described in JP 2000-105462 A.

Further, another method for the hydrophobic treatment involves: applying a liquid containing the above-described hydrophobic agent on the surface of the anodized film; and drying the liquid.

An application method used for the hydrophilic treatment or the hydrophobic treatment is not particularly limited. Examples thereof include bar coating, spin coating, spray coating, curtain coating, immersion coating, air knife coating, blade coating, and roll coating.

When the structural body of the present invention is used as a sample holder and a protein modified or decomposed by acid is used as a sample, neutralization treatment may be conducted for neutralizing the acid used in the anodizing treatment and remaining on the aluminum surface. The neutralization treatment may be conducted through a conventionally known method.

<Coefficient of Variation in Pore Size>

The thus-obtained structural body of the present invention has micropores having a coefficient of variation in pore size of 5 to 50%, preferably 10 to 20%. The coefficient of variation in pore size within the above range allows increased efficiency for sealing in the sealing treatment described below and the metal particles locating close to one another, thereby enhancing localized plasmon resonance.

The coefficient of variation (CV) in pore size is an index of variation in pore size and is defined by the following equation.

(Coefficient of variation in pore size)=(Standard deviation of pore size)/(Average pore size)

The coefficient of variation in pore size may be adjusted to 5 to 50% by controlling the degree of ordering property of the arrangement of micropores.

The degree of the ordering property of the arrangement can be evaluated by an average number of micropores present continuously on a straight line as an index.

To be specific, the average number of micropores present continuously on a straight line of less than 3 provides a coefficient of variation in pore size of 50% or more. The average number thereof of 3 or more and less than 5 provides a coefficient of variation in pore size of 20% or more and less than 50%. The average number thereof of 5 or more and less than 10 provides a coefficient of variation in pore size of 15% or more and less than 20%. The average number thereof of 10 or more and less than 15 provides a coefficient of variation in pore size of 10% or more and less than 15%. The average number thereof of 15 or more and less than 20 provides a coefficient of variation in pore size of 5% or more and less than 10%. The average number thereof of 20 or more provides a coefficient of variation in pore size of less than 5%.

<Sealing Treatment>

The structural body of the present invention has micropores of the anodized film sealed with a metal through the sealing treatment.

Figure 3:
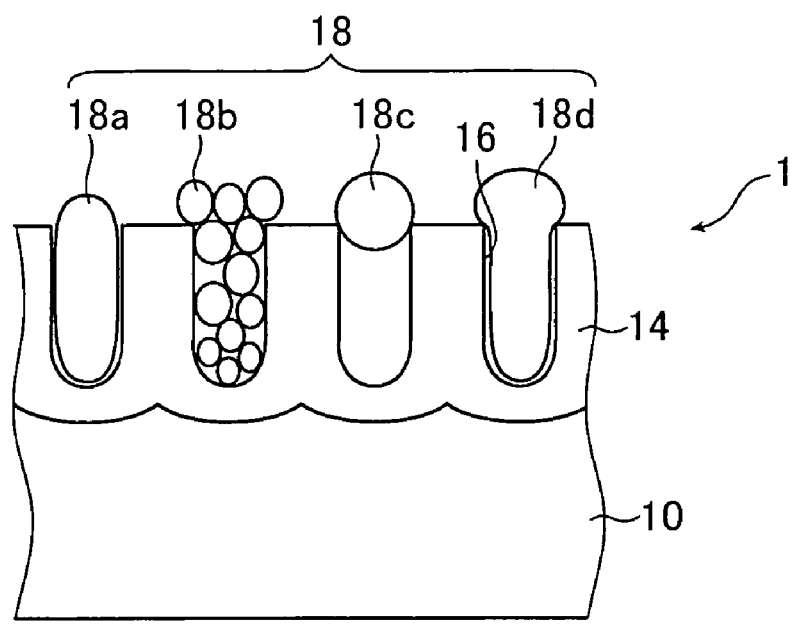
FIG. 3 is a schematic sectional view showing a structural body of the present invention.

FIG. 3 is a schematic sectional view showing a structural body of the present invention. In a structural body 1 shown in FIG. 3, the micropores 16 are sealed with a metal 18. The metal 18 is present on the surface of the anodized film 14 as particles.

Here, a sealing form is not particularly limited. The inside of a micropore may be completely filled with a metal (see metal 18a of FIG. 3), or the inside of the micropore may contain a space. For example, an opening of the micropore may be closed with a metal particle (see metal 18c of FIG. 3). The metal particle may have a size larger than that of the opening of the micropore (see metal 18d of FIG. 3), or may protrude from the surface of the anodized film. The inside of the micropore may be filled with one metal particle, or may be filled with metal particles (see metal 18b of FIG. 3).

The metal is an element having free electrons and metallic bonds. The metal is not particularly limited, and at least one of a metal element and an alloy may be used. When the structural body of the present invention is used as a sample holder for Raman scattering spectroscopic measurement, the metal preferably exhibits plasmon resonance. Of those, gold, silver, copper, nickel, and platinum are known to easily exhibit plasmon resonance (Chemistry Today, September 2003, pp. 20-27) and are preferable. Gold and silver are particularly preferable for easy electrodeposition or easy production of colloid particles.

When the structural body of the present invention is used as a magnetic recording medium, the metal is preferably a magnetic metal.

In the present invention, the magnetic metal refers to a single substance of a metal element having 3d electrons or 4f electrons on an outermost shell orbital or to an alloy thereof. Examples of the metal element include Fe, Co, Ni, Cr, Mn, Gd, Tb, Dy, Ho, Er, and Tm. Preferable examples of the alloy thereof include: an alloy of the metal element and at least one element selected from the group consisting of Au, Ag, Pt, and Pd which are noble metals having excellent anticorrosion property; an alloy of the metal element and Al and/or Cu having excellent electric conductivity; and magnetic alloys such as an Fe—Pt alloy, a Co—Pt alloy, a Co—Ni alloy, a Co—Cr alloy, Sm2Co17, 14Ni24Co8Al3Cu+Fe (alnico alloy), 78.5Ni+Fe (permalloy), 5Mo79Ni+Fe (supermalloy), and 50Co+Fe (permendur).

Of those, a single substance or an alloy of at least one element selected from the group consisting of Fe, Co, and Ni, is preferable. An Fe—Pt alloy, a Co—Pt alloy, and Ni are more preferable, and an Fe—Pt alloy having a ferromagnetic fct crystal structure is furthermore preferable from the viewpoint of high magnetic coercive force.

The method for the sealing treatment is not particularly limited, and a conventionally known method can be used. Preferable examples thereof include: electrodeposition; and a method involving applying a dispersion liquid of metal particles (metal element, alloy thereof, or colloid particles thereof) on an aluminum member having an anodized film and drying the dispersion liquid. The metal is preferably a single particle or an aggregate.

The electrodeposition may employ a conventionally known method. To be specific, gold electrodeposition involves: immersing an aluminum member in a dispersion liquid containing 1 g/L HAuCl$_4$ and 7 g/L H$_2$SO$_4$ at 30° C.; and conducting electrodeposition treatment at a constant voltage of 11 V (adjusted with a slidax) for 5 to 6 min.

An example of the electrodeposition using copper, tin, and nickel is described in detail in Chemistry Today, January 1997, pp. 51-54, and this method can be employed as well.

When the sealing treatment is conducted through electrodeposition using a magnetic metal, a preferable mode is a method using an electrolyte for nickel plating.

The electrolyte for nickel plating to be used may contain a nickel ion source, an anode dissolving agent, a pH buffer, and an additive.

Examples of the nickel ion source include nickel salts such as nickel sulfate, nickel chloride, and nickel sulfamate. The salt can be used alone or as a mixture of a plurality thereof.

Examples of the anode dissolving agent include ammonium chloride, nickel chloride, nickel bromide, and hydrochloric acid.

An example of the pH buffer includes boric acid.

An example of the additive includes a brightener. The brightener is an organic compound having a structure of =C—SO$_2$—, C=O, C=C, C=N, C=N, C=C, N—C=S, N=N, —CH$_2$—CH—O—, or the like. To be specific, 1,4-butyndiol is preferable.

The sealing treatment through electrodeposition causes variation in distance between metal particles to be formed due to variation in pore size. Thus, the metal particles may be partially located close to one another with relative ease. If the metal particles are partially close to one another, surface enhanced resonance Raman scattering can be utilized even if some metal particles are far away or are in contact with one another.

Meanwhile, the sealing treatment through electrodeposition on a conventional anodized film having a uniform pore size provides a uniform distance between the metal particles to be formed. Thus, the distance is hardly adjusted within a preferable range for the surface enhanced resonance Raman scattering. The distance falling out of the preferable range causes the metal particles to be present far away from one another or brings all the metal particles into contact with one another, and thus the surface enhanced resonance Raman scattering cannot be utilized.

The dispersion liquid used for a method using metal particles can be obtained through a conventionally known method. When the metal colloid particles are used, the dispersion liquid can be obtained through a production method for fine particles involving low vacuum evaporation, or through a production method for metal colloids involving reduction of an aqueous solution of a metal salt.

The metal colloid particles have an average particle size of preferably 1 to 200 nm, more preferably 1 to 100 nm, and furthermore preferably 2 to 80 nm.

Water is preferably used as a dispersion medium used for the dispersion liquid. Another example of the dispersion medium includes a mixed solvent of a solvent which may mix with water such as alcohol (including ethyl alcohol, n-propyl alcohol, i-propyl alcohol, 1-butyl alcohol, 2-butyl alcohol, t-butyl alcohol, Methyl Cellosolve, or Butyl Cellosolve), and water.

In the method using metal colloid particles, the application method is not particularly limited. Examples thereof include bar coating, spin coating, spray coating, curtain coating, immersion coating, air knife coating, blade coating, and roll coating.

Examples of the dispersion liquid preferably used for the method using metal colloid particles include a dispersion liquid of gold colloid particles and a dispersion liquid of silver colloid particles.

Examples of the dispersion liquid of gold colloid particles include: the dispersion liquids described in JP 2001-89140 A and JP 11-80647 A; and commercially available products.

The dispersion liquid of silver colloid particles preferably contains particles of an alloy of silver and palladium from the viewpoint of preventing an effect of acid eluting from the anodized film. In this case, the content of palladium is preferably 5 to 30 wt %.

The dispersion liquid is applied onto an aluminum member, and the resultant is arbitrarily washed using a solvent such as water. Thus, only particles filled into the micropores remain on the anodized film, and particles not filled into the micropores are removed.

The sealing treatment using metal particles except metal colloid particles such as particles of a metal element or an alloy can be conducted in substantially the same manner as that using the metal colloid particles.

The amount of a metal adhered to the aluminum surface after the sealing treatment is preferably 100 to 500 mg/m$^2$.

The surface porosity after the sealing treatment is preferably 20% or less. The surface porosity after the sealing treatment refers to a ratio of a total area of unsealed openings of micropores to an area of the aluminum surface. The surface porosity within the above range provides further enhanced localized plasmon resonance.

The metal colloid particles used for the dispersion liquid generally have variation in pore size distribution of about 10 to 20% as coefficient of variation. In the present invention, variation in pore size is adjusted to a specific range, to thereby efficiently use colloid particles having variation in pore size distribution for sealing.

When the pore size is 50 nm or more, the method using metal colloid particles is preferably employed. When the pore size is less than 50 nm, electrodeposition is preferably employed. Both methods are preferably combined and employed.

<Fine Structural Body>

The thus-obtained structural body of the present invention has micropores sealed with a metal, and the metal is present as particles on the surface of the anodized film.

In general, the distance between the metal particles is preferably small for increasing a Raman enhancing effect, but an optimum distance is affected by the size or shape of the metal particles. Further, depending on a molecular weight of a substance or a viscosity of a liquid used as a sample for Raman spectroscopic analysis, a problem may be caused in that the substance or the liquid may not sufficiently penetrate through the gaps among the metal particles.

Thus, the distance between the metal particles cannot be determined generally, but is in a range of preferably 1 to 400 nm, more preferably 5 to 300 nm, furthermore preferably 10 to 200 nm. The distance within the above range provides a large Raman enhancing effect and alleviates the problem in that the substance used as a sample does not penetrate through the gaps among the metal particles.

Here, "distance between metal particles" refers to the shortest distance between the surfaces of the adjacent particles.

<Raman Enhancing Effect by Localized Plasmon Resonance>

The Raman enhancing effect is a phenomenon of enhancing a Raman scattering intensity of a molecule adsorbed on a metal to about $10^5$ to $10^6$ times, so-called surface enhanced Raman scattering (SERS). Chemistry Today, September 2003, pp. 20-27 describes a Raman enhancing effect by localized plasmon resonance using metal particles of gold, silver, copper, platinum, nickel, or the like.

The structural body of the present invention can provide localized plasmon resonance with higher intensity than that of prior art. Thus, the structural body of the present invention may be used in Raman spectroscopic analysis to provide further increased Raman enhancing effect. Thus, the sample holder for Raman spectroscopic analysis employing the structural body of the present invention is useful.

Further, when the surface of the anodized film is subjected to surface treatment, the sample can be selectively and uniformly allowed to adhere to the surface of the metal particles by selecting the surface property in accordance with chemical properties of the sample.

In the report by Takayuki Okamoto, "Researches on interaction of metal nanoparticles and on biosensors" (supra), gold colloid particles are chemically fixed on a glass substrate using 3-aminopropyltrimethoxysilane. However, the inventors of the present invention have found a problem in that the gold colloid particles fixed on the glass substrate used for the sample holder for Raman spectroscopic analysis as a plasmon resonance device have poor reproducibility in signal intensity.

The inventors of the present invention have conducted intensive studies, and have found that when the plasmon resonance device is used for a sample holder for Raman spectroscopic analysis and when a liquid sample for analysis does not adhere to the surface of the metal particles or adheres thereto nonuniformly, a signal intensity may be small or reproducibility of the signal may be poor.

Further, the inventors of the present invention have found that in a device employing a self-ordered anodized film, a surface property selected from hydrophilic property and hydrophobic property may be imparted to the surface of the anodized film, and the device having one of the surface properties is selected in accordance with the chemical properties of the sample to be used for a sample holder for Raman spectroscopic analysis. Thus, the sample can be allowed to selectively and uniformly adhere to the surface of the metal particles. As a result, the signal intensity may be increased and reproducibility may be improved.

Thus, in a preferable mode of the structural body of the present invention, the surface of the anodized film has a surface property selected from hydrophilic property and hydrophobic property.

Figure 4:
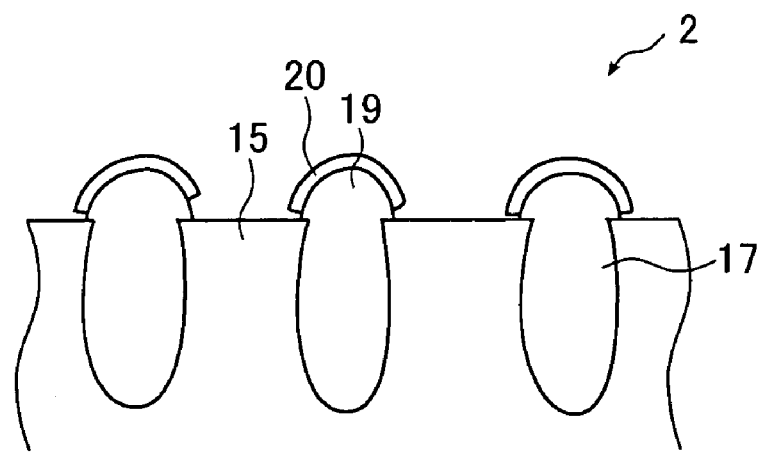
FIG. 4 is a schematic sectional view showing a surface of an example of a structural body of the present invention used as a sample holder for Raman spectroscopic analysis.

FIG. 4 is a schematic sectional view showing a surface of an example of a structural body of the present invention used as a sample holder for Raman spectroscopic analysis.

When the sample for Raman spectroscopic analysis is a hydrophilic substance, a structural body 2 having an anodized film 15 with a hydrophobic surface is preferably used. Alternatively, when the sample for Raman spectroscopic analysis is a hydrophobic substance, a structural body 2 having an anodized film 15 with a hydrophilic surface is preferably used. In this way, as shown in FIG. 4, a sample 20 is allowed to selectively and uniformly adhere to a surface of a particulate metal 19 formed on micropores 17.

The hydrophilic property and hydrophobic property of the sample will be described using amino acid as an example. Examples of hydrophilic molecules generally include: a molecule having a hydroxy group; a molecule having a charge; and a molecule having an acid amide group such as aspartic acid or glutamic acid. In contrast, examples of hydrophobic molecules include: a molecule having a hydrocarbon chain or an aromatic ring such as phenylalanine, tyrosine, or tryptophan; and a molecule having sulfur such as cystein or methionine.

In consideration of the properties of amino acid, the hydrophilic property/hydrophobic property of the surface of the anodized film is controlled such that a sample selectively adheres to the metal particles, to thereby improve the sensitivity.

Further, when neither the hydrophilic property nor the hydrophobic property is imparted to the surface of the anodized film, a trace amount of an airborne organic component or the like may adhere to the surface of the anodized film, to thereby change the surface property. To be specific, the surface of the anodized film may be hydrophilic just after formation of the anodized film, may have deteriorated hydrophilic property after several hours, and may be hydrophobic after several days.

Thus, when a structural body having no surface property imparted is used as a sample holder for Raman spectroscopic analysis, the amount of a sample to adhere to the surface of the metal particles may change with time. As a result, the Raman scattering intensity may change greatly. The structural body may need to be stored under vacuum or in a solvent such as alcohol for suppressing such change with time.

In contrast, when one surface property selected from the hydrophilic property and the hydrophobic property is imparted to the surface, the change with time is suppressed. Thus, the structural body has excellent time stability in Raman scattering intensity.

The usage of the sample holder for Raman spectroscopic analysis of the present invention is the same as that of a conventional sample holder for Raman spectroscopic analysis. To be specific, property of a substance in the vicinity of the metal held on the sample holder is detected by: irradiating the sample holder for Raman spectroscopic analysis of the present invention with light; and measuring the Raman scattering intensity of reflected light or transmitted light.

When the structural body of the present invention is used as a detector for light transmission Raman scattering, the structural body of the present invention is attached on an inner wall of an optically transparent vessel.

To be specific, a reacted solution is instantaneously injected into a transparent vessel through a flow injection method (flow method), to thereby easily analyze a structure change or the like of an easily modified substance such as a certain vitamin or a biological sample through ultrasensitive laser Raman analysis. Further, analysis of a trace amount of a reaction product is possible.

The structural body of the present invention can be applied to various flow injection analyses and the like.

The flow injection method has the following characteristics according to "Considerations on flow injection analysis" by Kyoji Toei, professor emeritus, Faculty of Science, Okayama University, published January 1999 (http://www.tokyokase-i.co.jp/kikou/bun/kikou101.html). The use of the structural body of the present invention for the flow injection method provides such advantages.

Flow injection analysis (FIA) is very useful for promoting automation in chemical analysis. The analysis generally involves: injecting an analysis sample into a reagent solution flowing through a narrow resin tube (such as Teflon tube) having an inner diameter of about 0.5 to 1.0 mm; mixing the analysis sample with the reagent for a reaction while the analysis sample flows through the narrow tube; and detecting, measuring, and determining a chemical species or a derivative thereof as an analysis target with a detector provided downstream. An FIA apparatus can be assembled easily by oneself by connecting main parts such as a feed pump, a sample injector, a reaction coil, and a detector. Almost all chemical analyses currently conducted can apply the FIA, thereby allowing automation. The following points are the characteristics and advantages of the FIA.

(1) Rapid measurement: Analysis of 100 to 200 samples per hour is reported, but an analysis rate of 30 to 60 samples per hour is generally employed.

(2) Easy operation: High quality analysis is possible with easy operation of simply injecting a sample. Skill is not required, and a novice can easily handle the operation.

(3) Reduction in amount of sample/reagent: The FIA generally requires about 100 µL of a sample at most. The FIA requires about 1 mL of the reagent in one measurement, which is $\frac{1}{10}$ to $\frac{1}{100}$ the amount required for manual analysis. Thus, the FIA can reduce the amount of waste liquid and significantly reduce environmental load. FIA is valued as a preferable analysis method from the viewpoint of zero-emission as well.

(4) High sensitivity/high precision: The FIA employs a high performance feed pump and can create a precisely controlled reaction field, to thereby attain analysis with high sensitivity and high precision.

<Magnetic Recording Medium>

The structural body of the present invention may be used as a magnetic recording medium when the metal is a magnetic metal.

To be specific, the structural body of the present invention can be applied to a recording medium for hard disk or a magnetic recording material based on alumina nanohole array (see "Research overview of the year 2002" published by Kanagawa Academy of Science and Technology, pp. 100-103) in combination with a magnetic head. The magnetic head is not particularly limited, and a conventionally known magnetic head can be used.

The structural body of the present invention allows high density recording when it is used as a magnetic recording medium, and is preferable from the viewpoint of realizing a small apparatus requiring small electric power. In particular, the colloid metals are preferably used as a filling metal from the viewpoint of high magnetic coercive force.

EXAMPLES

Hereinafter, the present invention will be described in more detail with reference to examples. However, the present invention is not limited thereto.

Examples 1 to 56 and Comparative Examples 1 to 5

1. Production of Support

As shown in Tables 1-1 to 2, a substrate was subjected to mirror finish treatment, pit formation, the anodizing treatment, and pore widening treatment, to thereby obtain a support. In Tables 1-1 to 2, "-" indicates that the corresponding treatment was not conducted.

TABLE 1-1

| | Substrate | Self-ordering anodizing treatment | Film removal treatment | Anodizing treatment | Pore widening treatment Treatment Liquid | Time [min] |
|---|---|---|---|---|---|---|
| Ex. 1 | 1 | 1 | 53 | 71 | — | — |
| Ex. 2 | 1 | 2 | 53 | 72 | — | — |
| Ex. 3 | 1 | 3 | 53 | 73 | — | — |
| Ex. 4 | 1 | 4 | 53 | 74 | 91 | 15 |
| Ex. 5 | 1 | 5 | 51 | 75 | 91 | 15 |
| Ex. 6 | 1 | 5 | 52 | 75 | 91 | 15 |
| Ex. 7 | 1 | 5 | 53 | 75 | 91 | 15 |
| Ex. 8 | 1 | 5 | 54 | 75 | 91 | 15 |
| Ex. 9 | 1 | 5 | 55 | 75 | 91 | 15 |
| Ex. 10 | 1 | 5 | 56 | 75 | 91 | 15 |
| Ex. 11 | 1 | 6 | 53 | 76 | 91 | 15 |
| Ex. 12 | 1 | 7 | 53 | 77 | 91 | 15 |
| Ex. 13 | 1 | 8 | 53 | 78 | 91 | 15 |
| Ex. 14 | 1 | 9 | 53 | 79 | 91 | 15 |
| Ex. 15 | 1 | 10 | 53 | 80 | 91 | 15 |
| Ex. 16 | 3 | 1 | 53 | 71 | — | — |
| Ex. 17 | 3 | 2 | 53 | 72 | — | — |
| Ex. 18 | 3 | 3 | 53 | 73 | — | — |
| Ex. 19 | 3 | 4 | 53 | 74 | 91 | 15 |
| Ex. 20 | 3 | 5 | 51 | 75 | 91 | 15 |
| Ex. 21 | 3 | 5 | 52 | 75 | 91 | 15 |

TABLE 1-2

| | Substrate | Self-ordering anodizing treatment | Film removal treatment | Anodizing treatment | Pore widening treatment Treatment Liquid | Time [min] |
|---|---|---|---|---|---|---|
| Ex. 22 | 3 | 5 | 53 | 75 | 91 | 15 |
| Ex. 23 | 3 | 5 | 54 | 75 | 91 | 15 |
| Ex. 24 | 3 | 5 | 55 | 75 | 91 | 15 |
| Ex. 25 | 3 | 5 | 56 | 75 | 91 | 15 |
| Ex. 26 | 3 | 6 | 53 | 76 | 91 | 15 |
| Ex. 27 | 3 | 7 | 53 | 77 | 91 | 15 |
| Ex. 28 | 3 | 8 | 53 | 78 | 91 | 15 |
| Ex. 29 | 3 | 9 | 53 | 79 | 91 | 15 |
| Ex. 30 | 3 | 10 | 53 | 80 | 91 | 15 |
| CE. 1 | 1 | — | — | 71 | 91 | 30 |
| CE. 2 | 1 | — | — | 75 | 91 | 30 |
| CE. 3 | 1 | — | — | 80 | 91 | 30 |

TABLE 2

| | Substrate | FIB method Pit density [pits/µm$^2$] | Distance between centers [nm] | Coefficient of variation | Anodizing treatment | Pore widening treatment Treatment Liquid | Time [min] |
|---|---|---|---|---|---|---|---|
| Ex. 31 | 2 | 100 | 100 | 0.05 | 73 | — | — |
| Ex. 32 | 2 | 100 | 100 | 0.1 | 73 | — | — |
| Ex. 33 | 2 | 100 | 100 | 0.1 | 73 | 91 | 15 |
| Ex. 34 | 2 | 100 | 100 | 0.1 | 73 | 91 | 30 |
| Ex. 35 | 2 | 100 | 100 | 0.1 | 73 | 91 | 45 |
| Ex. 36 | 2 | 100 | 100 | 0.3 | 73 | — | — |
| Ex. 37 | 2 | 100 | 100 | 0.5 | 73 | — | — |
| Ex. 38 | 4 | 100 | 100 | 0.1 | 73 | — | — |
| Ex. 39 | 5 | 100 | 100 | 0.1 | 73 | — | — |
| Ex. 40 | 6 | 100 | 100 | 0.1 | 73 | — | — |
| Ex. 41 | 7 | 100 | 100 | 0.1 | 73 | — | — |
| Ex. 42 | 8 | 1 | 1000 | 0.1 | 71 | — | — |
| Ex. 43 | 8 | 4 | 500 | 0.1 | 72 | — | — |
| Ex. 44 | 8 | 100 | 100 | 0.1 | 73 | — | — |
| Ex. 45 | 8 | 256 | 63 | 0.1 | 74 | 91 | 30 |
| Ex. 46 | 8 | 484 | 45 | 0.1 | 75 | 92 | 10 |
| Ex. 47 | 8 | 484 | 45 | 0.1 | 75 | 93 | 10 |
| Ex. 48 | 9 | 100 | 100 | 0.1 | 73 | — | — |
| Ex. 49 | 10 | 100 | 100 | 0.1 | 73 | — | — |
| Ex. 50 | 11 | 100 | 100 | 0.1 | 73 | — | — |
| Ex. 51 | 12 | 100 | 100 | 0.1 | 73 | — | — |
| CE. 4 | 7 | — | — | — | 73 | — | — |
| Ex. 52 | 2 | 100 | 100 | 0.1 | 73 | 91 | 15 |
| Ex. 53 | 2 | 100 | 100 | 0.1 | 73 | 91 | 30 |
| Ex. 54 | 8 | 256 | 63 | 0.1 | 74 | 91 | 30 |

TABLE 2-continued

|  | Substrate | FIB method | | | Anodizing treatment | Pore widening treatment | |
|---|---|---|---|---|---|---|---|
|  |  | Pit density [pits/μm²] | Distance between centers [nm] | Coefficient of variation |  | Treatment Liquid | Time [min] |
| Ex. 55 | 8 | 484 | 45 | 0.1 | 75 | 92 | 10 |
| Ex. 56 | 8 | 484 | 45 | 0.1 | 75 | 93 | 10 |
| CE. 5 | 7 | — | — | — | 73 | — | — |

Hereinafter, the substrate and each treatment will be described.

(1) Substrate

The following substrates were each used for production of a structural body.

Substrate 1: high purity aluminum, available from Wako Pure Chemical Industries, Ltd.; purity of 99.99 wt %; thickness of 0.4 mm Substrate 2: aluminum material JIS A1050 provided with a surface layer A, available from Nippon Light Metal Co., Ltd.; purity of 99.5 wt %; thickness of 0.24 mm Substrate 3: aluminum material JIS A1050 provided with a surface layer B, available from Nippon Light Metal Co., Ltd.; purity of 99.5 wt %; thickness of 0.24 mm Substrate 4: aluminum material JIS A1050, available from Nippon Light Metal Co., Ltd.; purity of 99.5 wt %; thickness of 0.30 mm Substrate 5: aluminum material JIS A1050 provided with a surface layer C, available from Nippon Light Metal Co., Ltd.; purity of 99.5 wt %; thickness of 0.30 mm Substrate 6: aluminum material JIS A1050 provided with a surface layer D, available from Nippon Light Metal Co., Ltd.; purity of 99.5 wt %; thickness of 0.30 mm Substrate 7: aluminum deposited film, Torayfan AT80, available from Toray Industries, Inc.; purity of 99.9 wt %; thickness of 0.02 mm Substrate 8: untreated aluminum XL material provided with a surface layer A, available from Sumitomo Light Metal Industries, Ltd.; purity of 99.3 wt %; thickness of 0.30 mm Substrate 9: glass provided with a surface layer E, available from As One Corporation; purity of 99.9 wt %; thickness of 5 mm Substrate 10: silicon wafer provided with a surface layer E, available from Shin-Etsu Chemical Co., Ltd.; purity of 99.99 wt % or more Substrate 11: synthetic quartz VIOSIL-SG-2B provided with a surface layer E, available from Shin-Etsu Chemical Co., Ltd.; purity of 99.99 wt % or more; thickness of 0.6 mm Substrate 12: copper-clad laminate (RAS33S42, available from Shin-Etsu Chemical Co., Ltd., unknown purity, thickness of 0.08 mm) provided with a surface layer E, having an Al—Cu alloy film on a surface through sputtering The aluminum material JIS A1050 had a regular reflectance of 40% in a longitudinal direction (standard deviation of 10%), a regular reflectance of 15% in a cross direction (standard deviation of 10%), and a purity of 99.5 wt % (standard deviation of 0.1 wt %).

The untreated aluminum XL material had a regular reflectance of 85% in a longitudinal direction (standard deviation of 5%), a regular reflectance of 83% in a cross direction (standard deviation of 5%), and a purity of 99.3 wt % (standard deviation of 0.1 wt %).

Further, the surface layers A to E are as described below.

The surface layer A was formed on a substrate through vacuum evaporation under the conditions of: an ultimate pressure of $4 \times 10^{-6}$ Pa; an evaporation current of 40 A; a substrate heated at 150° C.; and an evaporation material of an aluminum wire having 99.9 wt % purity (available from Nilaco Corporation). The surface layer A had a thickness of 0.2 μm.

The surface layer B was formed in the same manner as that of the surface layer A except that an aluminum wire having 99.99 wt % purity (available from Nilaco Corporation) was used as an evaporation material. The surface layer B had a thickness of 0.2 μm.

The surface layer C was formed on a substrate through sputtering under the conditions of: an ultimate pressure of $4 \times 10^{-6}$ Pa; a sputtering pressure of $10^{-2}$ Pa; an argon flow rate of 20 sccm; a substrate controlled at 150° C. (with cooling); no bias; a sputtering power source of RC; a sputtering electric power of RF400W; and a sputtering material of a 3N backing plate having 99.9 wt % purity (available from Kyodo International, Inc.). The surface layer C had a thickness of 0.5 μm.

The surface layer D was formed in the same manner as that of the surface layer A except that a 4N backing plate having 99.99 wt % purity (available from Kyodo International, Inc.) was used as a sputtering material. The surface layer D had a thickness of 0.5 μm.

The surface layer E was formed in the same manner as that of the surface layer A except that the surface layer E was formed to have a thickness of 1 μm.

The thickness of the surface layer was adjusted by: applying a masking to a PET substrate; conducting vacuum evaporation or sputtering with varying time under the same conditions as those described above; using a correlation calibration curve between time and film thickness measured with an atomic force microscope (AFM); and adjusting the time.

Further, the purity of the surface layer was determined by: conducting total quantitative analysis while digging the surface layer in a depth direction with an etching ion gun using a scanning X-ray photoelectron spectroscopic analyzer (Quantum 2000, manufactured by ULVAC-PHI, Inc.); and quantitatively determining contents of different metal elements through a calibration method. As a result, each surface layer had substantially the same purity as that of the evaporation material or the sputtering material.

(2) Mirror Finish Treatment

Of the substrates 1 to 12, the substrates 1 to 6 were subjected to the following mirror finish treatment.

<Mirror Finish Treatment>

The mirror finish treatment was conducted through polishing using a polishing cloth, buffing, and electrolytic polishing in the order given. After the buffing, the substrate was washed with water.

The polishing using a polishing cloth employed a grinder (Struers Abramin, manufactured by Marumoto Struers K. K.) and a water resistant polishing cloth (commercially available) while a thread size of the water resistant polishing cloth was changed to #200, #500, #800, #1000, and #1500 in the order given.

The buffing was conducted using a slurry polishing agent (FM No. 3 (average particle size of 1 μm) and FM No. 4 (average particle size of 0.3 μm), both available from Fujimi Incorporated).

The electrolytic polishing was conducted using an electrolyte having the following composition (at 70° C.), a substrate as an anode, and a carbon electrode as a cathode at a constant current density of 130 mA/cm$^2$ for 2 min. GP0110-30R (manufactured by Takasago, Ltd.) was used as a power source.

<Composition of Electrolyte>

| | |
|---|---|
| 85 wt % phosphoric acid (available from Wako Pure Chemical Industries, Ltd.) | 660 mL |
| Pure water | 160 mL |
| Sulfuric acid | 150 mL |
| Ethylene glycol | 30 mL |

(3) Pit Formation

Pits serving as starting points for micropore formation in the anodizing treatment described below were formed on the surface of each of the substrates 1 to 6 subjected to the mirror finish treatment and the substrates 7 to 12 without the mirror finish treatment through the following method (i) or (ii).

(i) Focused ion Beam Method

The surface of the substrate was irradiated with a focused ion beam using a focused ion beam system, to thereby form pits. Ga was used as an ion species, and an accelerating voltage was 30 kV. An ion beam diameter was about 30 nm, and an ion current was about 3 pA.

The irradiation was repeated by positioning pits using a secondary electron observation function of the focused ion beam system such that a pit density, a distance between the centers of the pits, and a coefficient of variation in distance between the centers of the pits were adjusted to the values representing a honeycomb pattern (closest packing structure) shown in Table 2. The retention time of the focused ion beam in each pit was about 10 msec.

(ii) Self-Ordering Method

Self-ordering anodizing treatment was conducted using the type, concentration, and temperature of electrolyte, a voltage, a current density, and a treatment time shown in Table 3, to thereby form an anodized film having a film thickness shown in Table 3. For the self-ordering anodizing treatment, Neo-Cool BD36 (manufactured by Yamato Scientific Co., Ltd.) was used as a cooler, and a pair stirrer PS-100 (manufactured by Tokyo Rikakikai Co., Ltd.) was used as a stirring apparatus under heating. GP0650-2R (manufactured by Takasago, Ltd.) was used as a power source.

TABLE 3

| Condition | Type of electrolyte | Concentration [mol/L] | Temperature [° C.] | Voltage [V] | Current density [A/dm$^2$] | Treatment time [hr] | Film thickness [μm] |
|---|---|---|---|---|---|---|---|
| 1 | Phosphoric acid | 0.3 | 0 | 195 | 0.25 | 8.0 | 40 |
| 2 | Phosphoric acid | 0.3 | 7 | 130 | 0.60 | 4.0 | 50 |
| 3 | Phosphoric acid | 1.0 | 7 | 80 | 0.50 | 4.0 | 40 |
| 4 | Phosphoric acid | 1.0 | 20 | 16 | 0.10 | 10.0 | 20 |
| 5 | Oxalic acid | 0.3 | 16 | 40 | 1.20 | 2.0 | 60 |
| 6 | Oxalic acid | 0.3 | 25 | 40 | 2.40 | 1.5 | 40 |
| 7 | Sulfuric acid | 0.3 | 0 | 27 | 1.20 | 3.5 | 50 |
| 8 | Sulfuric acid | 0.3 | 10 | 25 | 2.00 | 6.5 | 130 |
| 9 | Sulfuric acid | 0.3 | 16 | 25 | 3.00 | 1.0 | 15 |
| 10 | Sulfuric acid | 1.0 | 25 | 10 | 4.00 | 0.5 | 10 |

In Table 3, phosphoric acid, oxalic acid, and sulfuric acid used were all reagents available from Kanto Kagaku. The current densities shown are values in a stable state.

Next, the substrate having the anodized film formed thereon was immersed in a treatment liquid under the conditions shown in Table 4, to thereby conduct film removal treatment for dissolving the anodized film.

A film removal rate was calculated as described below from the change in film thickness of the anodized film with time and the treatment time. Table 4 shows the results. The film thickness of each anodized film after the film removal treatment was 0.1 μm or less.

<Calculation of Film Removal Rate>

The substrate sampled every hour during the film removal treatment was bent, and a side surface (broken surface) of a cracked portion of the substrate was observed using an ultra-high resolution SEM (Hitachi S-900, manufactured by Hitachi, Ltd.) at a relatively low accelerating voltage of 12 V and without evaporation treatment or the like for imparting electrical conductivity. Then, the film thickness was measured. The sampling was conducted by randomly selecting 10 positions in one sampling, and the film thickness was measured as an average of the 10 positions. An error of the film thickness fell within a range of ±10%.

TABLE 4

| Condition | 85 wt % phosphoric acid [g] | Chromic anhydride [g] | Pure water [g] | Temperature [° C.] | Film removal rate [μm/hr] |
|---|---|---|---|---|---|
| 51 | 100 | 30 | 1500 | 30 | 1 |
| 52 | 100 | 30 | 1500 | 50 | 4 |
| 53 | 75 | 30 | 1500 | 50 | 4 |
| 54 | 100 | 30 | 1500 | 70 | 8 |
| 55 | 100 | 30 | 1500 | 90 | 100 |
| 56 | 75 | 30 | 1500 | 90 | 100 |

Table 4, the 85 wt % phosphoric acid and chromic anhydride used were both reagents available from Kanto Kagaku.

The treatment liquids used in conditions 53 and 56 were compositions in accordance with JIS H8688(1998).

(4) The Anodizing Treatment

The substrate having pits formed thereon was subjected to the anodizing treatment. The anodizing treatment involved: immersing the substrate in an electrolyte; and subjecting the substrate to electrolysis once or multiple times under the conditions of the type, concentration, and temperature of electrolyte and a voltage for first electrolysis shown in Table 5.

When electrolysis is conducted multiple times, first electrolysis terminated when a constant voltage reached an initial set value $V_0$; second electrolysis terminated when a constant voltage reached an initial set value $0.9 \times V_0$ [V]; and third electrolysis terminated when a constant voltage reached an initial set value $0.8 \times V_0$ [V]. As described above, electrolysis was repeated multiple times until the nth time where a constant voltage reached an initial set value of $\{1-0.1 \times (n-1)\} \times V_0$.

Further, the thickness of the anodized film was measured in the same manner as that described above, and Table 5 shows an increased amount.

TABLE 5

| Condition | Type of electrolyte | Concentration [mol/L] | Temperature [° C.] | Voltage for first electrolysis [V] | Number of electrolysis treatment [times] | Increased amount of film thickness [μm] |
|---|---|---|---|---|---|---|
| 71 | Phosphoric acid | 0.3 | 0 | 195 | 8 | 0.2 |
| 72 | Phosphoric acid | 0.3 | 7 | 130 | 8 | 0.2 |
| 73 | Phosphoric acid | 1.0 | 7 | 80 | 7 | 0.2 |
| 74 | Phosphoric acid | 1.0 | 20 | 16 | 1 | 0.2 |
| 75 | Oxalic acid | 0.3 | 16 | 40 | 5 | 0.2 |
| 76 | Oxalic acid | 0.3 | 25 | 40 | 5 | 0.2 |
| 77 | Sulfuric acid | 0.3 | 0 | 40 | 5 | 0.2 |
| 78 | Sulfuric acid | 0.3 | 5 | 25 | 3 | 0.2 |
| 79 | Sulfuric acid | 0.3 | 16 | 25 | 3 | 0.4 |
| 80 | Sulfuric acid | 1.0 | 25 | 10 | 2 | 0.6 |

(5) Pore Widening Treatment

The pore widening treatment was conducted by immersing the substrate in a treatment liquid of the type, concentration, and temperature shown in Table 6 for a time period shown in Tables 1-1 to 2.

TABLE 6

| Condition | Type of treatment liquid | Concentration [g/L] | Temperature [° C.] |
|---|---|---|---|
| 91 | Phosphoric acid | 50 | 40 |
| 92 | Potassium hydroxide | 0.5 | 30 |
| 93 | Sodium hydroxide | 0.5 | 30 |

2. Properties of Support

The average pore size of micropores, coefficient of variation in pore size, average pore density, and pore area ratio (surface porosity before sealing) of the obtained support were measured through image analysis of an SEM surface photograph. The method for the image analysis is described below.

Binarization (Otsu method) was performed using image processing software (Image Factory, available from Asahi Hi-tech Co., Ltd.). Then, shape analysis of the binarized image was performed through black filling, black expansion, and black shrinkage in the order given. Then, the length displayed on the photograph was input using a measurement bar. Shape characteristics were extracted, and a black count and an equivalent circle diameter were output. The average pore density was calculated from the number of the black count, and the average pore size and the standard deviation were calculated from the distribution of the equivalent circle diameter. Further, the standard deviation was divided by the average pore size, to thereby determine the coefficient of variation in pore size. The surface porosity before sealing was calculated from the average pore size and the average pore density.

Tables 7-1 to 7-5 show the results.

3. Production of Structural Body

In each of Examples 1 to 51 and Comparative Examples 1 to 4, the obtained support was subjected to the following sealing treatment, to thereby obtain a structural body.

<Sealing Treatment 1 (Method Using Gold Colloid Particles)>

1.5 mL of a 1 wt % aqueous solution of citric acid was added to 1.5 mL of a 0.05 wt % aqueous $HAuCl_4$ solution. The mixture was gradually heated from room temperature using an alcohol lamp, and the heating was stopped when the color of the mixture changed to reddish purple. The mixture was cooled to room temperature to obtain a dispersion liquid of gold colloid particles (gold colloid particles having an average particle size of 120 nm). The support was immersed in the dispersion liquid for 1 min, washed with water, and then dried.

The support obtained in each of Example 52 to 56 and Comparative Example 5 was subjected to the following sealing treatment, to thereby obtain a structural body.

<Sealing Treatment 2 (Elecrodeposition)>

The support was immersed in a dispersion liquid containing 1 g/L $HAuCl_4$ and 7 g/L $H_2SO_4$ at 30° C. for electrodeposition at a constant voltage (adjusted by slidax) of 11 V for 5 to 6 min.

4. Properties of Structural Body (1) Surface Porosity

The surface porosity (surface porosity after sealing) of the obtained structural body was measured in the same manner as above.

Tables 7-1 to 7-5 show the results.

(2) Raman Enhancing Effect

A $3\times10^{-7}$ mol/L aqueous solution of Rhodamine 6G (available from Kanto Kagaku) and a 0.1 mol/L aqueous solution of NaCl (available from Kanto Kagaku) were applied onto the surface of the structural body. A Raman scattering intensity was measured using a Raman spectrophotometer (T64000, manufactured by HORIBA, Ltd.) at 1,660 $cm^{-1}$ under the conditions of an excitation wavelength of 488 nm and a Raman shift measurement range of 1,800 to 800 $cm^{-1}$.

The measured value of the Raman scattering intensity was divided by a value of Raman scattering intensity of a normal slide glass at 1,660 $cm^{-1}$ measured with a maximum laser output. Thus, the enhancement magnification was calculated, to thereby evaluate the Raman enhancing effect. When the sensitivity was too high, the laser output was reduced and the aqueous solution of Rhodamine 6G was diluted with water, to thereby calculate the enhancement magnification.

Tables 7-1 to 7-5 show the results.

Symbols in Tables 7-1 to 7-5 represent the following.

⊚: enhancement magnification of $10^5$ or more

○: enhancement magnification of $10^4$ or more and less than $10^5$

Δ: enhancement magnification of $10^2$ or more and less than $10^3$

×: enhancement magnification of less than $10^1$

TABLE 7-1

| | Average pore size [nm] | Average pore density [pores/μm²] | Coefficient of variation in pore size [%] | Surface porosity before sealing [%] | Surface porosity after sealing [%] | Raman enhancing effect |
|---|---|---|---|---|---|---|
| Example 1 | 500 | 1 | 5 | 40 | 0 | ⊚ |
| Example 2 | 300 | 5 | 5 | 30 | 0 | ⊚ |
| Example 3 | 100 | 20 | 8 | 20 | 5 | ⊚ |
| Example 4 | 25 | 800 | 10 | 20 | 10 | ○ |
| Example 5 | 20 | 1000 | 15 | 30 | 10 | ○ |
| Example 6 | 20 | 1000 | 15 | 30 | 10 | ○ |
| Example 7 | 20 | 1000 | 15 | 30 | 10 | ○ |
| Example 8 | 20 | 1000 | 15 | 30 | 10 | ○ |
| Example 9 | 20 | 1000 | 15 | 30 | 10 | ○ |
| Example 10 | 20 | 1000 | 15 | 30 | 10 | ○ |
| Example 11 | 20 | 1000 | 15 | 30 | 10 | ○ |
| Example 12 | 10 | 1000 | 15 | 20 | 5 | ○ |
| Example 13 | 10 | 1000 | 15 | 20 | 5 | ○ |
| Example 14 | 10 | 1000 | 15 | 20 | 5 | ○ |
| Example 15 | 8 | 1500 | 20 | 20 | 10 | Δ |

TABLE 7-2

| | Average pore size [nm] | Average pore density [pore/μm²] | Coefficient of variation in pore size [%] | Surface porosity before sealing [%] | Surface porosity after sealing [%] | Raman enhancing effect |
|---|---|---|---|---|---|---|
| Example 16 | 500 | 1 | 5 | 40 | 0 | ⊚ |
| Example 17 | 300 | 5 | 5 | 30 | 0 | ⊚ |
| Example 18 | 100 | 20 | 8 | 20 | 5 | ⊚ |
| Example 19 | 25 | 800 | 10 | 20 | 10 | ○ |
| Example 20 | 20 | 1000 | 15 | 30 | 10 | ○ |
| Example 21 | 20 | 1000 | 15 | 30 | 10 | ○ |
| Example 22 | 20 | 1000 | 15 | 30 | 10 | ○ |
| Example 23 | 20 | 1000 | 15 | 30 | 10 | ○ |
| Example 24 | 20 | 1000 | 15 | 30 | 10 | ○ |
| Example 25 | 20 | 1000 | 15 | 30 | 10 | ○ |
| Example 26 | 20 | 1000 | 15 | 30 | 10 | ○ |
| Example 27 | 10 | 1000 | 15 | 20 | 5 | ○ |
| Example 28 | 10 | 1000 | 15 | 20 | 5 | ○ |

TABLE 7-3

|  | Average pore size [nm] | Average pore density [pores/μm²] | Coefficient of variation in pore size [%] | Surface porosity before sealing [%] | Surface porosity after sealing [%] | Raman enhancing effect |
|---|---|---|---|---|---|---|
| Example 29 | 10 | 1000 | 15 | 20 | 5 | ○ |
| Example 30 | 8 | 1500 | 20 | 20 | 10 | Δ |
| Comparative Example 1 | 510 | 1 | 55 | 40 | 0 | x |
| Comparative Example 2 | 30 | 1000 | 70 | 30 | 10 | x |
| Comparative Example 3 | 15 | 1500 | 80 | 20 | 10 | x |
| Example 31 | 100 | 20 | 5 | 60 | 10 | ○ |
| Example 32 | 100 | 20 | 10 | 60 | 10 | ○ |
| Example 33 | 100 | 20 | 15 | 60 | 10 | ◎ |
| Example 34 | 100 | 20 | 20 | 60 | 10 | ◎ |
| Example 35 | 100 | 20 | 20 | 60 | 10 | ○ |
| Example 36 | 100 | 20 | 30 | 60 | 10 | ○ |

TABLE 7-4

|  | Average pore size [nm] | Average pore density [pores/μm²] | Coefficient of variation in pore size [%] | Surface porosity before sealing [%] | Surface porosity after sealing [%] | Raman enhancing effect |
|---|---|---|---|---|---|---|
| Example 37 | 100 | 20 | 50 | 60 | 10 | ○ |
| Example 38 | 100 | 20 | 10 | 60 | 10 | ○ |
| Example 39 | 100 | 20 | 10 | 60 | 10 | ○ |
| Example 40 | 100 | 20 | 10 | 60 | 10 | ○ |
| Example 41 | 100 | 20 | 10 | 60 | 10 | ○ |
| Example 42 | 500 | 1 | 10 | 40 | 20 | ○ |
| Example 43 | 300 | 5 | 10 | 50 | 15 | ○ |
| Example 44 | 100 | 20 | 10 | 60 | 10 | ○ |
| Example 45 | 60 | 180 | 15 | 60 | 0 | ◎ |
| Example 46 | 40 | 400 | 15 | 60 | 0 | ◎ |
| Example 47 | 40 | 400 | 15 | 60 | 0 | ◎ |

TABLE 7-5

|  | Average pore size [nm] | Average pore density [pores/μm²] | Coefficient of variation in pore size [%] | Surface porosity before sealing [%] | Surface porosity after sealing [%] | Raman enhancing effect |
|---|---|---|---|---|---|---|
| Example 48 | 100 | 20 | 10 | 60 | 10 | ○ |
| Example 49 | 100 | 20 | 10 | 60 | 10 | ○ |
| Example 50 | 100 | 20 | 10 | 60 | 10 | ○ |
| Example 51 | 100 | 20 | 10 | 60 | 10 | ○ |
| Comparative Example 4 | 100 | 20 | 70 | 60 | 10 | x |
| Example 52 | 100 | 20 | 15 | 60 | 0 | ◎ |
| Example 53 | 100 | 20 | 20 | 60 | 0 | ◎ |
| Example 54 | 60 | 180 | 15 | 60 | 0 | ◎ |
| Example 55 | 40 | 400 | 15 | 60 | 0 | ◎ |
| Example 56 | 40 | 400 | 15 | 60 | 0 | ◎ |
| Comparative Example 5 | 100 | 20 | 70 | 60 | 10 | x |

Tables 7-1 to 7-5 clearly show that the structural body of the present invention has an excellent Raman enhancing effect.

Example 57

A structural body was produced in the same manner as in Example 1 except that the sealing treatment was conducted as described below.

<Sealing Treatment 3 (Method Using Dispersion Liquid of Fe—Pt Magnetic Particles)>

The following operation was conducted in a high purity Ar gas, to thereby produce a dispersion liquid of magnetic particles.

First, 0.64 mmol of iron (III) acetylacetonate [$CH_3COCH=C(O-)CH_3$]$_3$Fe, 1.5 mmol of 1,2-hexadecanediol, and 20 mL of dioctyl ether were mixed, and the mixture was heated at 100° C. Then, 0.5 mmol of oleic acid and 0.5 mmol of oleylamine were added thereto, and the mixture was refluxed at 200° C. for 30 min, to thereby obtain a liquid A.

Meanwhile, 0.5 mmol of platinum (II) acetylacetonate [$CH_3COCH=C(O-)CH_3$]$_2$Pt, 1.5 mmol of 1,2-hexadecandiol, and 20 mL of dioctyl ether were mixed, and the mixture was heated at 100° C. The mixture was cooled to room temperature, to thereby obtain a liquid B.

The liquid A was added to the cooled liquid B, and the mixture was refluxed at 297° C. for 30 min. After the mixture was cooled, 40 mL of ethanol was added. A precipitate was settled, and a supernatant was then removed.

0.16 mmol of oleic acid and 0.15 mmol of oleylamine were added to the mixture. 25 mL of hexane was added for dispersion. Then, 20 mL of ethanol was added thereto. A precipitate was settled, and a supernatant was then removed.

Further, 0.16 mmol of oleic acid and 0.15 mmol of oleylamine were added to the mixture. 20 mL of hexane was added for dispersion. Then, 15 mL of ethanol was added thereto. A precipitate was settled, and a supernatant was then removed.

Further, 0.16 mmol of oleic acid and 0.15 mmol of oleylamine were added to the mixture. 20 mL of hexane was added for dispersion, to thereby obtain a nanodispersed liquid having Fe—Pt magnetic particles dispersed therein (dispersion liquid of magnetic particles).

The thus-obtained dispersion liquid of magnetic particles was placed on a mesh for TEM observation and dried, to thereby prepare a TEM sample. The TEM sample was observed using a transmission electron microscope (TEM, Hitachi, Ltd.) at an accelerating voltage of 300 kV. The results confirmed the presence of magnetic particles having an average diameter of about 5 nm.

The following operation was conducted using the dispersion liquid of the magnetic particles obtained as described above under an $N_2$ atmosphere.

That is, the dispersion liquid of the magnetic particles was applied onto the surface of the support of 50 mm-square through spin coating such that the amount of magnetic particles was 0.5 mg/m$^2$, and the liquid was dried. Then, for prevention of deformation, both surfaces of the support were sandwiched by mirror-finished SUS 304 materials, and a weight was placed thereon with a load of 1 kgf/50 mm-square. The resultant was heated (annealed) in an electric furnace at 350° C. for 30 min, to thereby obtain a structural body serving as a magnetic recording medium.

The thus-obtained structural body as a magnetic recording medium was evaluated for magnetic properties. To be specific, the magnetic coercive force (Hc) was measured in an applied magnetic field of 790 kA/m (10 kOe) using a high sensitivity magnetic vector measurement device (manufactured by Toei Industry Co., Ltd.) and a DATA processor (manufactured by Toei Industry Co., Ltd.). As a result, the magnetic coercive force Hc was 300 kA/m.

Examples 58 to 62

A structural body was produced in the same manner as in Example 1 except that the sealing treatment was conducted as described below.

<Sealing Treatment 4 (Electrodeposition)>

The support was immersed in a bath of an electrolyte for nickel plating containing components shown in Table 8, and at a pH and a temperature shown in Table 8. The support was subjected to electrodeposition at a cathode current density shown in Table 8 for 2.5 min, to thereby obtain a structural body as a magnetic recording medium. Table 8 shows whether or not the bath was stirred during electrodeposition. In Table 8, "air stirring" refers to a method involving: feeding air to a bottom of an electrolytic tank; and causing convection in the electrolyte by buoyancy of elevating air bubbles for stirring. This method has a feature that nonuniform treatment due to flow rate hardly occurs compared with "stirring" using a propeller.

The structural body as a magnetic recording medium was evaluated for the magnetic properties as in the same manner as that described above. Table 8 shows the results.

TABLE 8

|  | Example 58 | Example 59 | Example 60 | Example 61 | Example 62 |
|---|---|---|---|---|---|
| Nickel sulfate [g/L] | 150 | 240 | — | — | — |
| Nickel chloride [g/L] | — | 45 | 30 | 240 | 350 |
| Nickel sulfamate [g/L] | — | — | 400 | — | — |
| Ammonium chloride [g/L] | 15 | — | — | — | — |
| Nickel bromide [g/L] | — | — | 50 | — | — |
| Hydrochloric acid [mL/L] | — | — | — | 125 | — |
| Boric acid [g/L] | 15 | 35 | 30 | — | 35 |
| Additive  Type | — | 1,4-butynediol | 1,4-butynediol | — | — |
|   Amount [g/L] | — | 0.2 | 0.2 | — | — |
| pH | 6.0 | 4.0 | 4.0 | 1.2 | 1.5 |
| Bath temperature [° C.] | Normal temperature | 45 | 60 | Normal temperature | 65 |

TABLE 8-continued

|  | Example 58 | Example 59 | Example 60 | Example 61 | Example 62 |
|---|---|---|---|---|---|
| Cathode current density [A/dm$^2$] | 0.8 | 4 | 10 | 8 | 2 |
| Stirring | None | Air stirring | Stirring | None | Stirring |
| Hc [kA/m] | 400 | 500 | 500 | 500 | 500 |

Table 8 clearly shows that the structural body of the present invention as a magnetic recording medium has a large magnetic coercive force.

Examples 63 to 80

1. Production of Structure

A substrate was sequentially subjected to mirror finish treatment, pit formation, the anodizing treatment, pore widening treatment, surface treatment, and sealing treatment as shown in Tables 9 and 10, to thereby obtain a structural body. In Table 9 to 10, "-" indicates that the corresponding treatment was not conducted.

flow rate of 20 sccm; a substrate controlled at 150° C. (with cooling); no bias; a sputtering power supply of RC; a sputtering electric power of RF400W; and a sputtering material of 4N backing plate having 99.99 wt % purity (available from Kyodo International, Inc.). The surface layer had a thickness of 0.5 μm.

The adjustment method for the thickness of the surface layer, the measurement method for the purity of the surface layer, and the results thereof were the same as those described above.

TABLE 9

|  | Substrate | Self-ordering anodizing treatment | Anodizing treatment | Surface treatment | Sealing treatment | Coefficient of variation in pore size [%] |
|---|---|---|---|---|---|---|
| Example 63 | 1 | 101 | 1 | Hydrophilic treatment | 1 | 8 |
| Example 64 | 1 | 101 | 1 | Hydrophobic treatment 1 | 1 | 8 |
| Example 65 | 1 | 101 | 1 | Hydrophobic treatment 2 | 1 | 8 |
| Example 66 | 1 | 102 | 2 | Hydrophilic treatment | 2 | 10 |
| Example 67 | 1 | 102 | 2 | Hydrophobic treatment 1 | 2 | 10 |
| Example 68 | 1 | 102 | 2 | Hydrophobic treatment 2 | 2 | 10 |
| Example 69 | 1 | 101 | 3 | — | 1 | 8 |
| Example 70 | 1 | 102 | 4 | — | 2 | 10 |
| Example 71 | 1 | 101 | 5 | — | 1 | 8 |
| Example 72 | 1 | 102 | 6 | — | 2 | 10 |
| Example 73 | 1 | 101 | 7 | — | 1 | 8 |
| Example 74 | 1 | 102 | 8 | — | 2 | 10 |

TABLE 10

|  | Substrate | FIB method Pit density [pits/μm$^2$] | FIB method Distance between centers [nm] | Anodizing treatment | Sealing treatment | Coefficient of variation in pore size [%] |
|---|---|---|---|---|---|---|
| Example 75 | 13 | 100 | 100 | 3 | 2 | 10 |
| Example 76 | 13 | 100 | 100 | 4 | 2 | 10 |
| Example 77 | 13 | 100 | 100 | 5 | 2 | 10 |
| Example 78 | 13 | 100 | 100 | 6 | 2 | 10 |
| Example 79 | 13 | 100 | 100 | 7 | 2 | 10 |
| Example 80 | 13 | 100 | 100 | 8 | 2 | 10 |

Hereinafter, the substrate and each treatment will be described.

(1) Substrate

The substrate used for the production of the structural body is described below.

Substrate 1: substrate 1 used above

Substrate 13: glass provided with a surface layer, available from As One Corporation, thickness of 5 mm The surface layer of the substrate 13 was formed through sputtering on glass under the conditions of: an ultimate pressure of $4 \times 10^{-6}$ Pa; a sputtering pressure of $10^{-2}$ Pa; an argon (2) Mirror Finish Treatment Of the substrates 1 and 13, the substrate 1 was subjected to mirror finish treatment in the same manner as that described above.

(3) Pit Formation

Pits serving as starting points for micropore formation during anodizing treatment described below were formed on the surface of the substrate 1 subjected to the mirror finish treatment and the surface of the substrate 13 without the mirror finish treatment through the following method (i) or (ii).

(i) Focused ion Beam Method

The pits were formed through irradiation of the surface of the substrate 13 with a focused ion beam in the same manner as that described above.

(ii) Self-Ordering Method

Self-ordering anodizing treatment was conducted on the surface of the substrate 1 using the type, concentration, and temperature of electrolyte, a voltage, a current density, and a treatment time shown in Table 11, to thereby form an anodized film having a film thickness and an average pore size shown in Table 11. For the self-ordering anodizing treatment, NeoCool BD36 (manufactured by Yamato Scientific Co., Ltd.) was used as a cooler, and a pair stirrer PS-100 (manufactured by Tokyo Rikakikai Co., Ltd.) was used as a stirring apparatus under heating. GP0650-2R (manufactured by Takasago, Ltd.) was used as a power source.

immersing the substrate in an electrolyte (at a liquid temperature shown in Table 12) prepared by adding a treatment agent shown in Table 12 in an amount shown in Table 12 into a 1 mol/L aqueous solution of phosphoric acid; and subjecting the substrate to electrolysis once or multiple times at a voltage for first electrolysis shown in Table 12.

When electrolysis is conducted multiple times, first electrolysis terminated when a constant voltage reached an initial set value $V_0$; second electrolysis terminated when a constant voltage reached an initial set value $0.9 \times V_0$ [V]; and third electrolysis terminated when a constant voltage reached an initial set value $0.8 \times V_0$ [V]. As described above, the electrolysis was repeated multiple times until the nth time where a constant voltage reached an initial set value of $\{1-0.1 \times (n-1)\} \times V_0$.

TABLE 11

| Condition | Type of electrolyte | Concentration [mol/L] | Temperature [° C.] | Voltage [V] | Current density [mA/dm$^2$] | Time [hr] | Film thickness [μm] | Average pore size [nm] |
|---|---|---|---|---|---|---|---|---|
| 101 | Phosphoric acid | 1 | 7 | 80 | 400 | 8 | 40 | 100 |
| 102 | Phosphoric acid | 1 | 20 | 16 | 100 | 20 | 20 | 20 |

In Table 11, phosphoric acid used was a reagent available from Kanto Kagaku. The current density represents a value in a stable state.

The average pore size of micropores was measured through image analysis of an SEM surface photograph. A method for the image analysis is described below.

Binarization (Otsu method) was performed using image processing software (Image Factory, available from Asahi Hi-tech Co., Ltd.). Then, shape analysis of the binarized image was performed through black filling, black expansion, and black shrinkage in the order given. Then, the length displayed on the photograph was input using a measurement bar. Shape characteristics were extracted, and the equivalent circle diameter was output. The average pore size was calculated from the distribution of the equivalent circle diameter.

The substrate having the anodized film formed thereon was subjected to film removal treatment for dissolving the anodized film under the condition 52.

The film removal rate was calculated as described above from the change in film thickness of the anodized film with time and the treatment time, resulting in 4 μm/hr. The thickness of the anodized film after the film removal treatment was 0.1 μm or less.

(4) The Anodizing Treatment

The substrate having pits formed thereon was subjected to the anodizing treatment. The anodizing treatment involved:

The treatment agents are as described below.

Hydrophilic agent 1: colloidal silica, SNOWTEX ST-O, available from Nissan Chemical Industries, Ltd.; $SiO_2$ content of 20 wt %; particle size of 10 to 20 μm; pH of 2.0 to 4.0

Hydrophilic agent 2: colloidal alumina, ALUMINASOL 200, available from Nissan Chemical Industries, Ltd.; $Al_2O_3$ content of 10 wt %; $CH_3COOH$ content of 3.5 wt % or less; feather-like; stabilized by acetic acid Hydrophobic agent: modified styrene/butadiene copolymer-based latex, Nipol LX407AS, available from ZEON Corporation; average particle size of 100 to 140 nm; pH of 5 to 6

The thickness of the anodized film was measured in the same manner as that described above, and Table 12 shows an increased amount thereof.

Further, a water droplet (droplet diameter of 2 mm) was dropped onto a surface of the anodized film in air 24 hours and 1 month after the formation of the anodized film. After 30 sec, an angle (contact angle of water droplet in air) between the surface of the anodized film and the surface of the water droplet was measured using a contact angle meter (CA-S150, manufactured by Kyowa Interface Science Co., Ltd.). The measurement was conducted on 5 different points on the sample, and an average was determined.

Table 12 shows the results. In Table 12, "extended wetting" indicates high wetting and change in shape of the water droplet to extend until the measurement such that the contact angle could not be measured.

TABLE 12

| Condition | Type of treatment agent | Addition amount [wt %] | Temperature [° C.] | Voltage [V] | Number of electrolysis treatment [times] | Increased amount of film thickness [μm] | Contact angle after 24 hours [°] | Contact angle after 1 month [°] |
|---|---|---|---|---|---|---|---|---|
| 1 | None | — | 7 | 80 | 7 | 0.2 | 5 | 40 |
| 2 | None | — | 20 | 16 | 1 | 0.2 | 5 | 40 |
| 3 | Hydrophilic agent 1 | 5 | 7 | 80 | 7 | 0.2 | Extended wetting | Extended wetting |
| 4 | Hydrophilic agent 1 | 20 | 20 | 16 | 1 | 0.2 | Extended wetting | Extended wetting |
| 5 | Hydrophilic agent 2 | 5 | 7 | 80 | 7 | 0.2 | Extended wetting | Extended wetting |
| 6 | Hydrophilic agent 2 | 20 | 20 | 16 | 1 | 0.2 | Extended wetting | Extended wetting |
| 7 | Hydrophobic agent | 5 | 7 | 80 | 7 | 0.2 | 90 | 90 |
| 8 | Hydrophobic agent | 20 | 20 | 16 | 1 | 0.2 | 90 | 90 |

(5) Pore Widening Treatment

The pore widening treatment was conducted by immersing the substrate in an aqueous solution of phosphoric acid (at a liquid temperature of 30° C.) in a concentration of 50 g/L for 30 min.

(6) Surface Treatment

The surface treatment involved one treatment selected from the group consisting of hydrophilic treatment, hydrophobic treatment 1, and hydrophobic treatment 2.

The hydrophilic treatment was conducted by immersing a surface of the anodized film in a 2.5 wt % aqueous solution of sodium silicate No. 3 (at a liquid temperature of 30° C.) for 10 sec.

The hydrophobic treatment 1 was conducted by applying and drying a treatment liquid (at a liquid temperature of 25° C.) having the following composition such that the application amount was 2 mg/m² after drying.

<Composition of Treatment Liquid>

| β-alanine (available from Kanto Kagaku) | 0.2 g |
|---|---|
| Methanol | 100 g |
| Water | 1 g |

The hydrophobic treatment 2 was conducted by applying and drying a methanol solution of $CF_3CF_2CH_2CH_2Si(OCH_2CH_3)_3$ (SIH5814.2, available from Chisso Corporation) such that the application amount was 2 mg/m² after drying.

(7) Sealing Treatment

The sealing treatment involved one of the sealing treatment 1 and the sealing treatment 2.

2. Properties of Anodized Film

After the surface treatment, the coefficient of variation in pore size of the micropores of the anodized film was measured before the sealing treatment in the same manner as that described above.

Tables 9 and 10 show the results.

3. Measurement of Raman Enhancing Effect

One of the following samples A to D was applied on the surface of the structural body to prepare a measurement sample. Then, the Raman scattering intensity was measured using a Raman spectrophotometer (T64000, manufactured by HORIBA, Ltd.) in the Raman shift measurement ranges (cm⁻¹) as specified below. 50 measurement samples were prepared for each of Experiments, and a Raman scattering intensity of each sample was measured.

Sample A: aqueous D-glucose solution (available from Kanto Kagaku); high hydrophilic property; excitation wavelength of 457 nm; measurement wave number of 285 $cm^{-1}$; Raman shift measurement range of 100 to 500 $cm^{-1}$ Sample B: aqueous lactose solution (available from Kanto Kagaku); low hydrophilic property; excitation wavelength of 710 nm; measurement wave number of 992 $cm^{-1}$; Raman shift measurement range of 200 to 2,000 $cm^{-1}$ Sample C: aqueous pyridine solution (available from Kanto Kagaku); low hydrophobic property; excitation wavelength of 710 nm; measurement wave number of 1,036 $cm^{-1}$; Raman shift measurement range of 200 to 2,000 $cm^{-1}$ Sample D: methanol solution of Rhodamine 6G (available from Kanto Kagaku); high hydrophobic property; excitation wavelength of 710 nm; measurement wave number of 1,655 $cm^{-1}$; Raman shift measurement range of 200 to 2,000 $cm^{-1}$ An average value of the measured values of the Raman scattering intensity was divided by a value of Raman scattering intensity of a normal slide glass measured with a maximum laser output. Thus, the enhancement magnification was calculated, and the magnitude of Raman enhancing effect was evaluated.

Further, the coefficient of variation (CV) in values of the measured Raman scattering intensity was calculated, and reproducibility of the Raman enhancing effect was evaluated. The coefficient of variation is defined by the following equation.

(Coefficient of variation in Raman scattering intensity)=(Standard deviation of Raman scattering intensity)/(Average Raman scattering intensity)

The measurement of the Raman scattering intensity was conducted 24 hours and 1 month after the production of the structural body, to thereby evaluate the stability of the Raman enhancing effect with time.

Tables 13-1 and 13-2 show the results.

Symbols for the "magnitude of Raman enhancing effect" in Tables 13-1 and 13-2 represent the following.

⊚: enhancement magnification of $10^5$ or more

○: enhancement magnification of $10^4$ or more and less than $10^5$

Δ: enhancement magnification of $10^2$ or more and less than $10^3$

×: enhancement magnification of less than $10^1$

Symbols for the "reproducibility of Raman enhancing effect" in Tables 13-1 and 13-2 represent the following.

◎: coefficient of variation of 10% or less

○: coefficient of variation of more than 10% and 25% or less

Δ: coefficient of variation of more than 25% and 50% or less

×: coefficient of variation of more than 50%

(FeSO$_4$·7H$_2$O). While the mixture was maintained at 20° C. and stirred, a 10 wt % aqueous solution of silver nitrate and palladium nitrate (molar ratio of 9:1) was added thereto at a rate of 200 mL/min. Then, the mixture was repeatedly centrifuged and washed with water, and pure water was added thereto to a final concentration of 3 wt %, to thereby obtain a dispersion liquid of silver colloid particles. The particle size of the silver colloid particles was measured through TEM observation, resulting in about 9 to 12 nm.

Isopropyl alcohol was added to 100 g of the obtained dispersion liquid of silver colloid particles, and the mixture

TABLE 13-1

| | Structural body | Sample | After 24 hours | | After 1 month | |
|---|---|---|---|---|---|---|
| | | | Magnitude of Raman enhancing effect | Reproducibility of Raman enhancing effect | Magnitude of Raman enhancing effect | Reproducibility of Raman enhancing effect |
| Experiment 1 | Example 69 | C | ◎ | ○ | ◎ | ○ |
| Experiment 2 | Example 69 | D | ◎ | ○ | ◎ | ○ |
| Experiment 3 | Example 70 | C | ◎ | ○ | ◎ | ○ |
| Experiment 4 | Example 70 | D | ◎ | ○ | ◎ | ○ |
| Experiment 5 | Example 71 | C | ◎ | ○ | ◎ | ○ |
| Experiment 6 | Example 71 | D | ◎ | ○ | ◎ | ○ |
| Experiment 7 | Example 72 | C | ◎ | ○ | ◎ | ○ |
| Experiment 8 | Example 72 | D | ◎ | ○ | ◎ | ○ |
| Experiment 9 | Example 73 | A | ○ | ○ | ○ | ○ |
| Experiment 10 | Example 73 | B | ○ | ○ | ○ | ○ |
| Experiment 11 | Example 74 | A | ◎ | ○ | ◎ | ○ |
| Experiment 12 | Example 74 | B | ◎ | ○ | ◎ | ○ |
| Experiment 13 | Example 63 | C | ◎ | ○ | ◎ | ○ |
| Experiment 14 | Example 66 | D | ◎ | ○ | ◎ | ○ |
| Experiment 15 | Example 64 | A | ○ | ○ | ○ | ○ |
| Experiment 16 | Example 67 | B | ◎ | ○ | ◎ | ○ |
| Experiment 17 | Example 65 | A | ○ | ◎ | ○ | ◎ |

TABLE 13-2

| | Structural body | Sample | After 24 hours | | After 1 month | |
|---|---|---|---|---|---|---|
| | | | Magnitude of Raman enhancing effect | Reproducibility of Raman enhancing effect | Magnitude of Raman enhancing effect | Reproducibility of Raman enhancing effect |
| Experiment 18 | Example 68 | B | ◎ | ◎ | ◎ | ◎ |
| Experiment 19 | Example 65 | C | ○ | ◎ | ○ | ◎ |
| Experiment 20 | Example 68 | D | ◎ | ◎ | ◎ | ◎ |
| Experiment 21 | Example 75 | C | ◎ | ○ | ◎ | ○ |
| Experiment 22 | Example 76 | C | ◎ | ○ | ◎ | ○ |
| Experiment 23 | Example 77 | D | ◎ | ○ | ◎ | ○ |
| Experiment 24 | Example 78 | D | ◎ | ○ | ◎ | ○ |
| Experiment 25 | Example 79 | B | ○ | ○ | ○ | ○ |
| Experiment 26 | Example 80 | B | ◎ | ○ | ◎ | ○ |

Tables 13-1 and 13-2 clearly show that the structural body of the present invention having the anodized film with a hydrophilic surface or a hydrophobic surface is excellent in the magnitude of Raman enhancing effect, reproducibility thereof, and stability thereof with time.

A structural body was produced in the same manner as in Examples 1 to 51, 63 to 65, 69 to 71, and 73, and Comparative Examples 1 to 4 except that the sealing treatment was conducted as follows. Then, the structural body was evaluated for properties.

<Sealing Treatment 5 (Method Using Silver Colloid Particles)>

A 40 wt % aqueous solution of citric acid was added and mixed into a 30 wt % aqueous solution of iron (II) sulfate was subjected to ultrasonic dispersion. Then, the mixture was filtered through a propylene filter having a pore size of 1 μm, to thereby obtain an application liquid of silver colloid particles.

The use of the silver colloid particles provided the same Raman enhancing effect as that obtained by the use of the gold colloid particles.

What is claimed is:

1. A structural body including at least partially an aluminum member having on a surface an anodized film with micropores present, in which: the micropores have a coefficient of variation in pore size of 5 to 50%; and the micropores are each sealed with a metal; the anodized film has a thickness of 0.1 to 1 μm; the micropores have an average pore size of 0.01 to 0.5 μm and an average pore density of 50 to 150 pores/$\mu m^2$; the micropores collectively account for an area ratio of 20 to 50%; and the structural body has a surface porosity of 20% or less.

2. The structural body according to claim 1, in which the metal is present on the surface of the anodized film as particles.

3. The structural body according to claim 1, in which a surface of the anodized film has a surface property selected from hydrophilic property and hydrophobic property.

4. The structural body according to claim 1, in which the metal is one of a single particle and an aggregate and is produced through one of an electrodeposition method and a method involving applying a dispersion liquid of metal particles and drying the applied liquid.

5. The structural body according to claim 1, in which the aluminum member has an aluminum purity of 99.5 wt % or more.

6. The structural body according to claim 1, in which the metal is one of gold and silver.

7. The structural body according to claim 1, in which the metal is a magnetic metal.

8. The structural body according to claim 7, in which the magnetic metal is one of a single substance and an alloy of at least one element selected from the group consisting of Fe, Co, and Ni.

9. A method of producing the structural body according to claim 1, including the steps of: forming pits on a surface of the aluminum member; subjecting the aluminum member to anodizing treatment for forming the anodized film having the micropores at positions of the pits; and filling the metal into the micropores for sealing.

10. The method of producing a structural body according to claim 9, in which the step of forming pits on a surface of the aluminum member is conducted through anodizing treatment.

11. The method of producing a structural body according to claims 10, in which, in the step of forming pits on a surface of the aluminum member, the anodized film formed through the anodizing treatment has a thickness of 10 to 50 $\mu m$.

12. A sample holder for Raman spectroscopic analysis comprising the structural body according to claim 1.

13. A magnetic recording medium comprising the structural body according to claim 7.

* * * * *